United States Patent
Leimbach et al.

(10) Patent No.: US 10,786,249 B2
(45) Date of Patent: Sep. 29, 2020

(54) SURGICAL STAPLER WITH ROTARY CAM DRIVE

(71) Applicant: ETHICON LLC, Guaynabo, PR (US)

(72) Inventors: Richard L. Leimbach, Cincinnati, OH (US); Richard F. Schwemberger, Cincinnati, OH (US); John P. Measamer, Cincinnati, OH (US); Johnny H. Alexander, III, West Chester, OH (US); Christopher C. Miller, Loveland, OH (US); Brian F. DiNardo, Cincinnati, OH (US); Jason M. Rector, Maineville, OH (US)

(73) Assignee: Ethicon LLC, Guaynabo, PR (US)

( * ) Notice: Subject to any disclaimer, the term of this patent is extended or adjusted under 35 U.S.C. 154(b) by 275 days.

(21) Appl. No.: 15/632,894

(22) Filed: Jun. 26, 2017

(65) Prior Publication Data
US 2017/0354409 A1    Dec. 14, 2017

Related U.S. Application Data

(63) Continuation of application No. 14/033,763, filed on Sep. 23, 2013, now Pat. No. 9,713,469.

(51) Int. Cl.
| A61B 17/068 | (2006.01) |
| A61B 17/115 | (2006.01) |
| A61B 17/00 | (2006.01) |

(52) U.S. Cl.
CPC ........ A61B 17/068 (2013.01); A61B 17/1155 (2013.01); *A61B 2017/00367* (2013.01); *A61B 2017/00398* (2013.01)

(58) Field of Classification Search
CPC .............. A61B 17/068; A61B 17/1155; A61B 2017/00367; A61B 2017/00398
(Continued)

(56) References Cited

U.S. PATENT DOCUMENTS 2,030,571 A * 2/1936 Cawley ................. F16K 31/524
                                                    74/833
2,211,741 A * 8/1940 Elwell .................... B25D 17/04
                                                    173/121
(Continued)

FOREIGN PATENT DOCUMENTS

| CN | 1649547 A | 8/2005 |
| CN | 101991449 A | 3/2011 |

(Continued)

OTHER PUBLICATIONS

Partial European Search Report and Written Opinion dated Feb. 11, 2015 for Application No. 14185832.4.
(Continued)

*Primary Examiner* — Dariush Seif
(74) *Attorney, Agent, or Firm* — Frost Brown Todd LLC

(57) ABSTRACT

A surgical circular stapler has a handle assembly, a shaft, a stapling assembly, a motor, a drive assembly, and a firing assembly. The shaft extends distally from the handle assembly. The stapling assembly is secured to a distal end of the shaft. Longitudinal translation of the firing assembly causes the stapling assembly to drive a plurality of staples in a circular array to secure two lumens of tissue together. The stapling assembly may further drive a blade to sever any excess tissue interior of the circular array of staples. The motor is operable to rotate the drive assembly to thereby translate the firing assembly. A resilient member biases the firing assembly proximally. Through cooperation between the firing assembly and the resilient member, the firing assembly is driven distally and proximally to complete a firing stroke in response to rotation of the drive assembly through a single revolution.

20 Claims, 30 Drawing Sheets

(58) Field of Classification Search
USPC ............ 227/175.1–182.1; 606/75, 219, 220; 73/53–56, 567, 569
See application file for complete search history.

(56) References Cited

U.S. PATENT DOCUMENTS

| | | | |
|---|---|---|---|
| 2,892,570 A * | 6/1959 | Thoresen | G01F 15/001 222/20 |
| 3,556,061 A * | 1/1971 | Schmidt | F01L 1/181 123/90.27 |
| 3,610,218 A * | 10/1971 | Durham | F01L 1/185 123/90.25 |
| 3,815,476 A * | 6/1974 | Green | A61B 17/0684 227/130 |
| 3,974,705 A * | 8/1976 | Wittkamp | B23B 9/00 74/53 |
| 4,152,953 A * | 5/1979 | Headley | F01L 1/14 123/90.48 |
| 4,289,041 A * | 9/1981 | Valdespino | B25F 3/00 173/121 |
| 4,644,952 A * | 2/1987 | Patipa | A61M 37/0076 173/205 |
| 4,805,823 A | 2/1989 | Rothfuss | |
| 5,205,459 A | 4/1993 | Brinkerhoff et al. | |
| 5,224,390 A * | 7/1993 | Tysver | F16H 25/04 74/10.29 |
| 5,249,583 A * | 10/1993 | Mallaby | A61B 10/0275 600/567 |
| 5,253,546 A * | 10/1993 | Elrod | F01L 1/08 123/90.6 |
| 5,271,544 A | 12/1993 | Fox et al. | |
| 5,275,322 A | 1/1994 | Brinkerhoff et al. | |
| 5,285,945 A | 2/1994 | Brinkerhoff et al. | |
| 5,292,053 A | 3/1994 | Bilotti et al. | |
| 5,333,773 A | 8/1994 | Main et al. | |
| 5,337,623 A * | 8/1994 | Huang | B23Q 3/1554 74/53 |
| 5,350,104 A | 9/1994 | Main et al. | |
| 5,415,334 A | 5/1995 | Williamson, IV et al. | |
| 5,465,895 A | 11/1995 | Knodel et al. | |
| 5,533,661 A | 7/1996 | Main et al. | |
| 5,597,107 A | 1/1997 | Knodel et al. | |
| 5,628,446 A * | 5/1997 | Geiste | A61B 17/0684 227/175.1 |
| 5,632,432 A | 5/1997 | Schulze et al. | |
| 5,673,840 A | 10/1997 | Schulze et al. | |
| 5,704,534 A | 1/1998 | Huitema et al. | |
| 5,814,055 A | 9/1998 | Knodel et al. | |
| 5,816,471 A | 10/1998 | Plyley et al. | |
| 6,021,573 A * | 2/2000 | Kikuchi | B23D 49/02 30/392 |
| 6,042,607 A * | 3/2000 | Williamson, IV | A61B 17/0469 606/151 |
| 6,050,472 A * | 4/2000 | Shibata | A61B 17/115 227/175.2 |
| 6,058,815 A * | 5/2000 | Habermehl | B25B 21/00 81/177.1 |
| 6,073,503 A * | 6/2000 | Matsuno | B65B 65/02 74/53 |
| 6,443,973 B1 * | 9/2002 | Whitman | A61B 17/07207 606/219 |
| 6,471,713 B1 * | 10/2002 | Vargas | A61B 17/11 606/153 |
| 6,698,177 B1 * | 3/2004 | Akehi | B21D 53/28 56/236 |
| 6,945,444 B2 | 9/2005 | Gresham et al. | |
| 6,978,921 B2 | 12/2005 | Shelton, IV et al. | |
| 7,000,818 B2 | 2/2006 | Shelton, IV et al. | |
| 7,134,508 B2 * | 11/2006 | Prell | B23D 51/16 173/29 |
| 7,143,923 B2 | 12/2006 | Shelton, IV et al. | |
| 7,178,244 B2 * | 2/2007 | Fossella | B26B 5/00 30/162 |
| 7,303,108 B2 | 12/2007 | Shelton, IV et al. | |
| 7,367,485 B2 | 5/2008 | Shelton, IV et al. | |
| 7,380,695 B2 | 6/2008 | Doll et al. | |
| 7,380,696 B2 | 6/2008 | Shelton, IV et al. | |
| 7,404,508 B2 | 7/2008 | Smith et al. | |
| 7,422,136 B1 | 9/2008 | Marczyk | |
| 7,434,715 B2 | 10/2008 | Shelton, IV et al. | |
| 7,556,185 B2 * | 7/2009 | Viola | A61B 17/07207 227/175.1 |
| 7,721,930 B2 | 5/2010 | McKenna et al. | |
| 7,770,775 B2 * | 8/2010 | Shelton, IV | A61B 17/07207 227/178.1 |
| 7,794,475 B2 | 9/2010 | Hess et al. | |
| 7,959,050 B2 | 6/2011 | Smith et al. | |
| 8,025,199 B2 * | 9/2011 | Whitman | A61B 17/115 227/155 |
| 8,028,885 B2 * | 10/2011 | Smith | A61B 17/1114 227/179.1 |
| 8,408,439 B2 | 4/2013 | Huang et al. | |
| 8,453,914 B2 | 6/2013 | Laurent et al. | |
| 8,459,524 B2 | 6/2013 | Pribanic | |
| 8,720,289 B2 * | 5/2014 | Howard | F16H 25/122 74/56 |
| 8,910,847 B2 | 12/2014 | Nalagatla et al. | |
| 9,161,803 B2 | 10/2015 | Yates et al. | |
| 9,232,945 B2 * | 1/2016 | Zingman | A61B 17/072 |
| 9,289,207 B2 | 3/2016 | Shelton, IV | |
| 9,498,222 B2 | 11/2016 | Scheib et al. | |
| 9,532,783 B2 | 1/2017 | Swayze et al. | |
| 9,572,573 B2 | 2/2017 | Scheib et al. | |
| 9,597,081 B2 | 3/2017 | Swayze et al. | |
| 9,713,469 B2 | 7/2017 | Leimbach et al. | |
| 9,724,100 B2 * | 8/2017 | Scheib | A61B 17/1155 |
| 9,907,552 B2 | 3/2018 | Measamer et al. | |
| 2007/0175955 A1 * | 8/2007 | Shelton, IV | A61B 17/07207 227/178.1 |
| 2007/0175957 A1 * | 8/2007 | Shelton, IV | A61B 17/07207 227/178.1 |
| 2009/0270895 A1 * | 10/2009 | Churchill | A61B 1/303 606/170 |
| 2010/0252610 A1 * | 10/2010 | Viola | A61B 17/07207 227/177.1 |
| 2011/0036888 A1 * | 2/2011 | Pribanic | A61B 17/068 227/175.1 |
| 2011/0261666 A1 | 10/2011 | Vlutters et al. | |
| 2012/0116379 A1 * | 5/2012 | Yates | A61B 17/00234 606/33 |
| 2013/0211397 A1 * | 8/2013 | Parihar | A61B 18/18 606/33 |
| 2013/0220220 A1 * | 8/2013 | Bassat | B05C 13/00 118/503 |
| 2013/0304069 A1 * | 11/2013 | Bono | A61B 17/1624 606/80 |
| 2014/0158747 A1 | 6/2014 | Measamer et al. | |
| 2014/0305992 A1 * | 10/2014 | Kimsey | A61B 17/068 227/176.1 |
| 2015/0083772 A1 * | 3/2015 | Miller | A61B 17/1155 227/175.1 |
| 2015/0083774 A1 * | 3/2015 | Measamer | A61B 17/068 227/175.1 |
| 2015/0083775 A1 * | 3/2015 | Leimbach | A61B 17/1155 227/175.1 |
| 2016/0076406 A1 * | 3/2016 | Cobb | F16H 21/28 123/90.6 |
| 2016/0223057 A1 * | 8/2016 | Murphy | F15B 15/06 |

FOREIGN PATENT DOCUMENTS

| | | |
|---|---|---|
| EP | 1 992 296 | 11/2008 |
| EP | 2 025 293 | 2/2009 |
| RU | 2098025 C1 | 12/1997 |
| WO | WO 97/30659 | 8/1997 |

(56) References Cited

FOREIGN PATENT DOCUMENTS

| WO | WO 03/079911 | 10/2003 |
| WO | WO 2014/099703 A2 | 6/2014 |

OTHER PUBLICATIONS

European Search Report dated Jun. 17, 2015 for Application No. EP 14185832.4, 12 pgs.

International Search Report dated Mar. 25, 2015 for Application No. PCT/US2014/056510, 9 pgs.

International Preliminary Report on Patentability and Written Opinion dated Mar. 29, 2016 for Application No. PCT/US2014/056510, 13 pgs.

Japanese Office Action, Notification of Reasons for Refusal, and Search Report dated Apr. 27, 2018 for Application No. JP 2016-544009, 42 pgs.

Brazilian Office Action dated Feb. 2, 2020 for Application No. BR 112016006299-0, 4 pgs.

Chinese Office Action, The First Office Action, and First Search dated Jun. 26, 2018 for Application No. 201480052188.2, 13 pages.

European Communication dated Aug. 12, 2016 for Application No. 14185832.4, 4 pages.

European Decision to Grant dated Mar. 15, 2018 for Application No. 14185832.4, 2 pages.

Japanese Notice of Grant dated Jul 24, 2018 for Application No. 2016-544009, 2 pages.

Russian Office Action and Search Report dated May 21, 2018 for Application No. 2016115719, 8 pages.

Pokrovskyi, P.I., (ed.) The Encyclopedical Dictionary of Medical Terms, Moscow Medicine, 2001, p. 330 (Reference unavailable. Please consider as prior art until proven otherwise.).

Fedorov, I.V., (ed.) The Surgical Instruments, Functions and Purposes Thereof, Adelaida, Multipurpose project agency, Kazan, 2001, p. 10, par. 1. (Reference unavailable. Please consider as prior art until proven otherwise.).

* cited by examiner

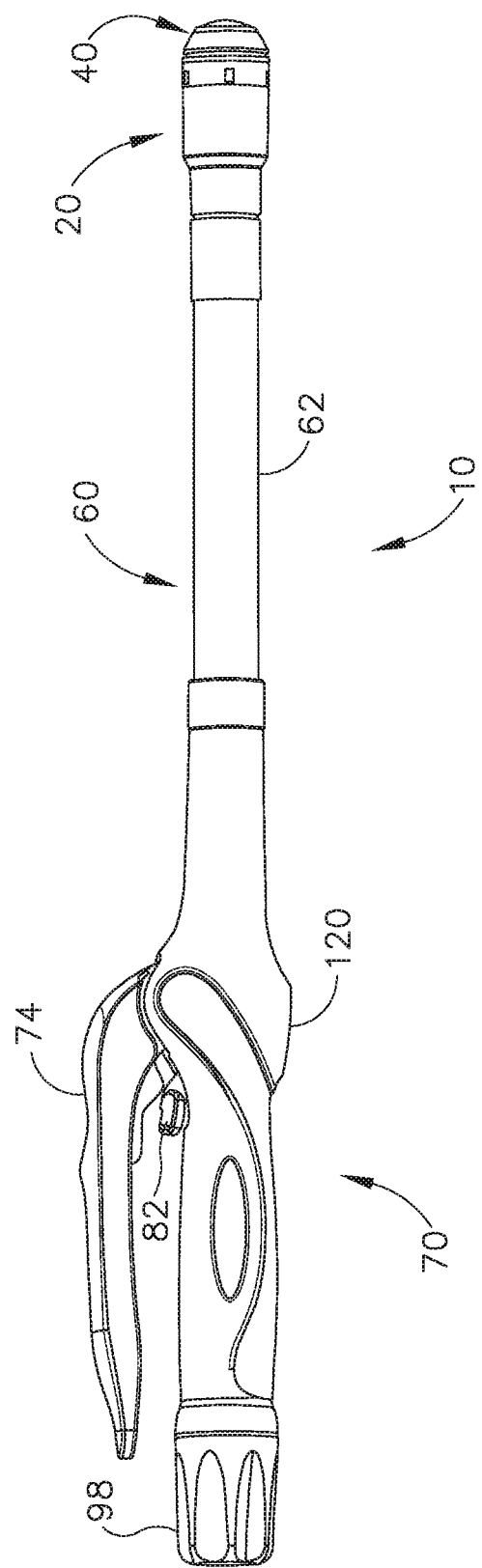

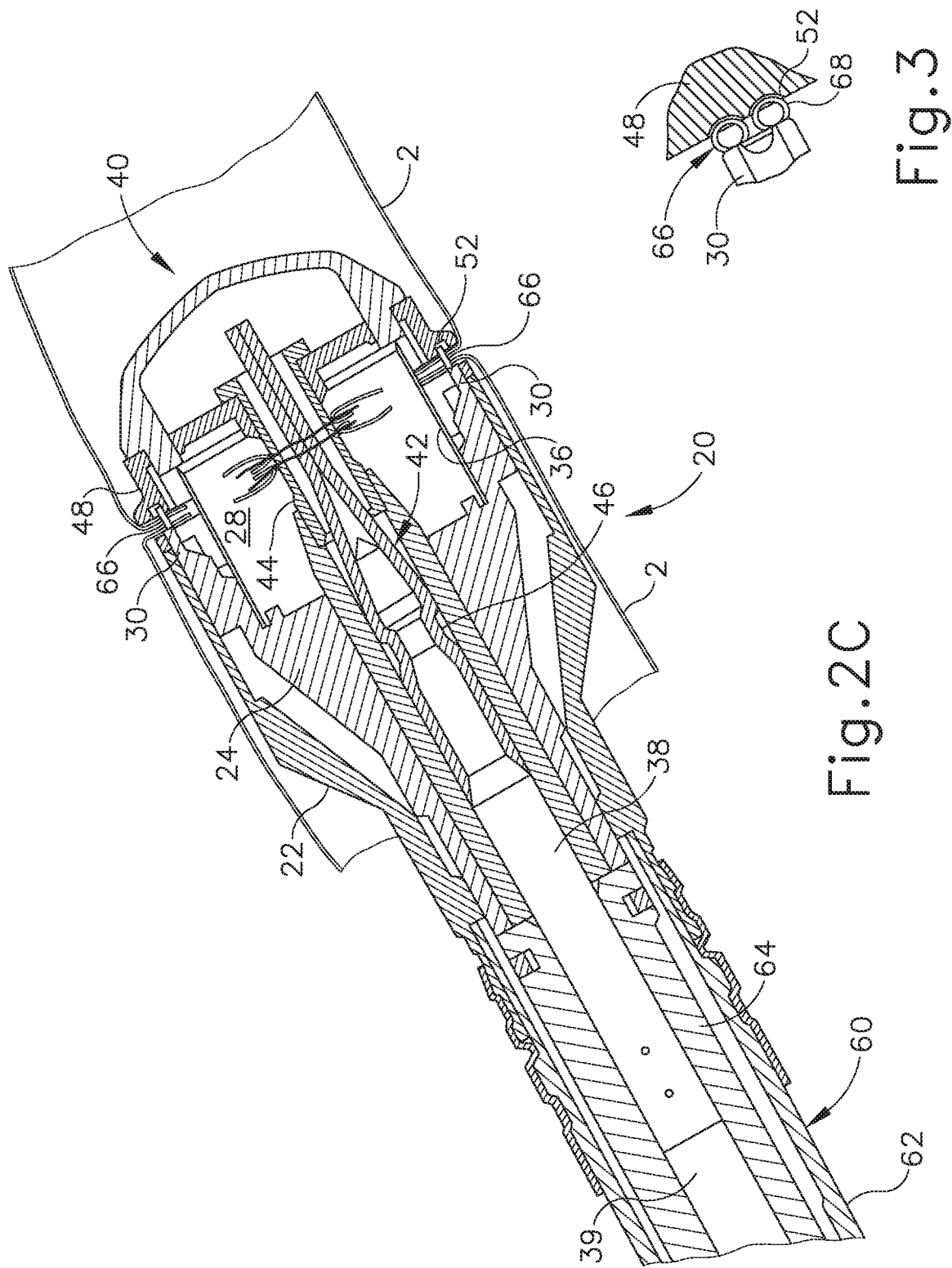

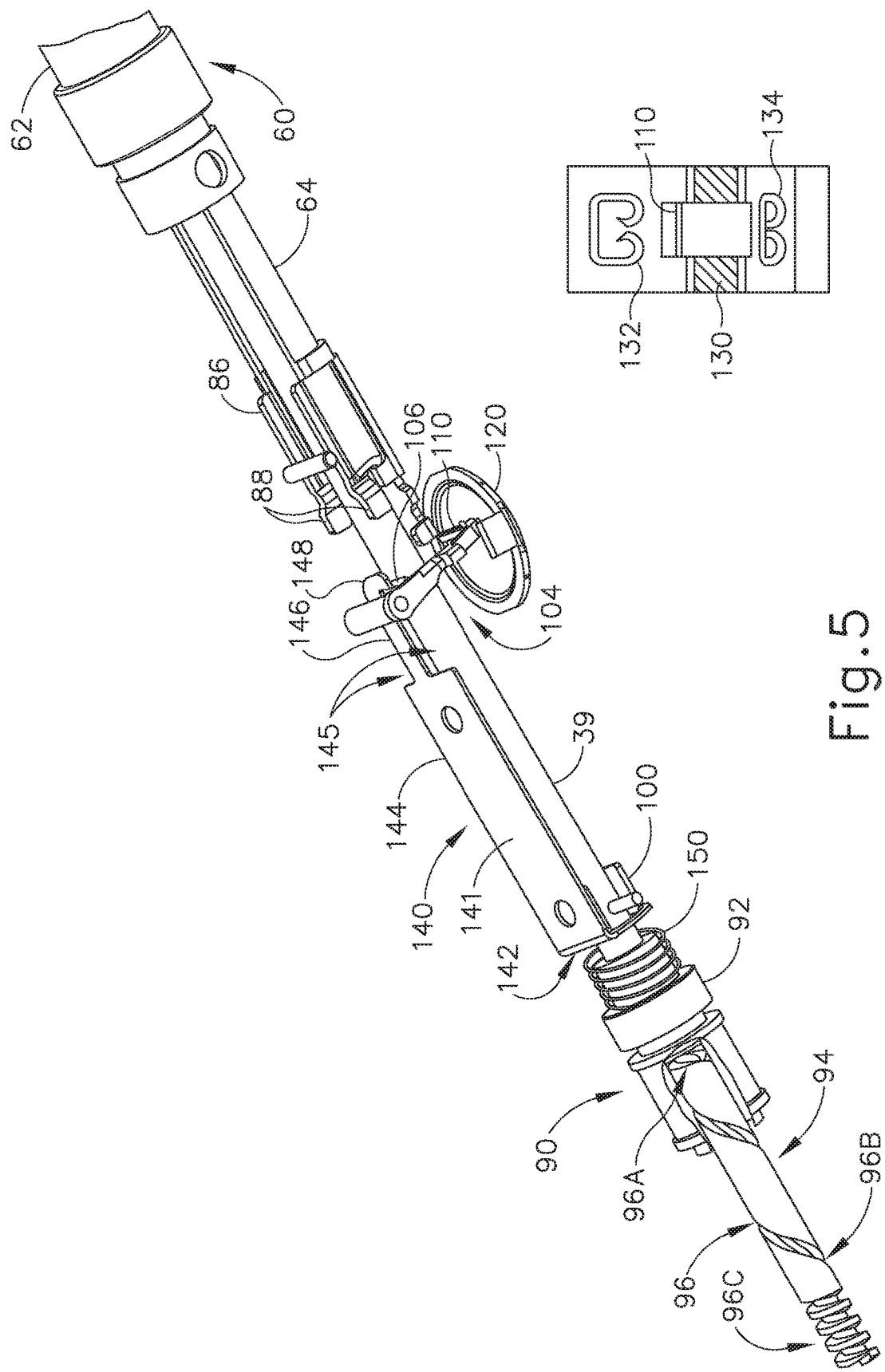

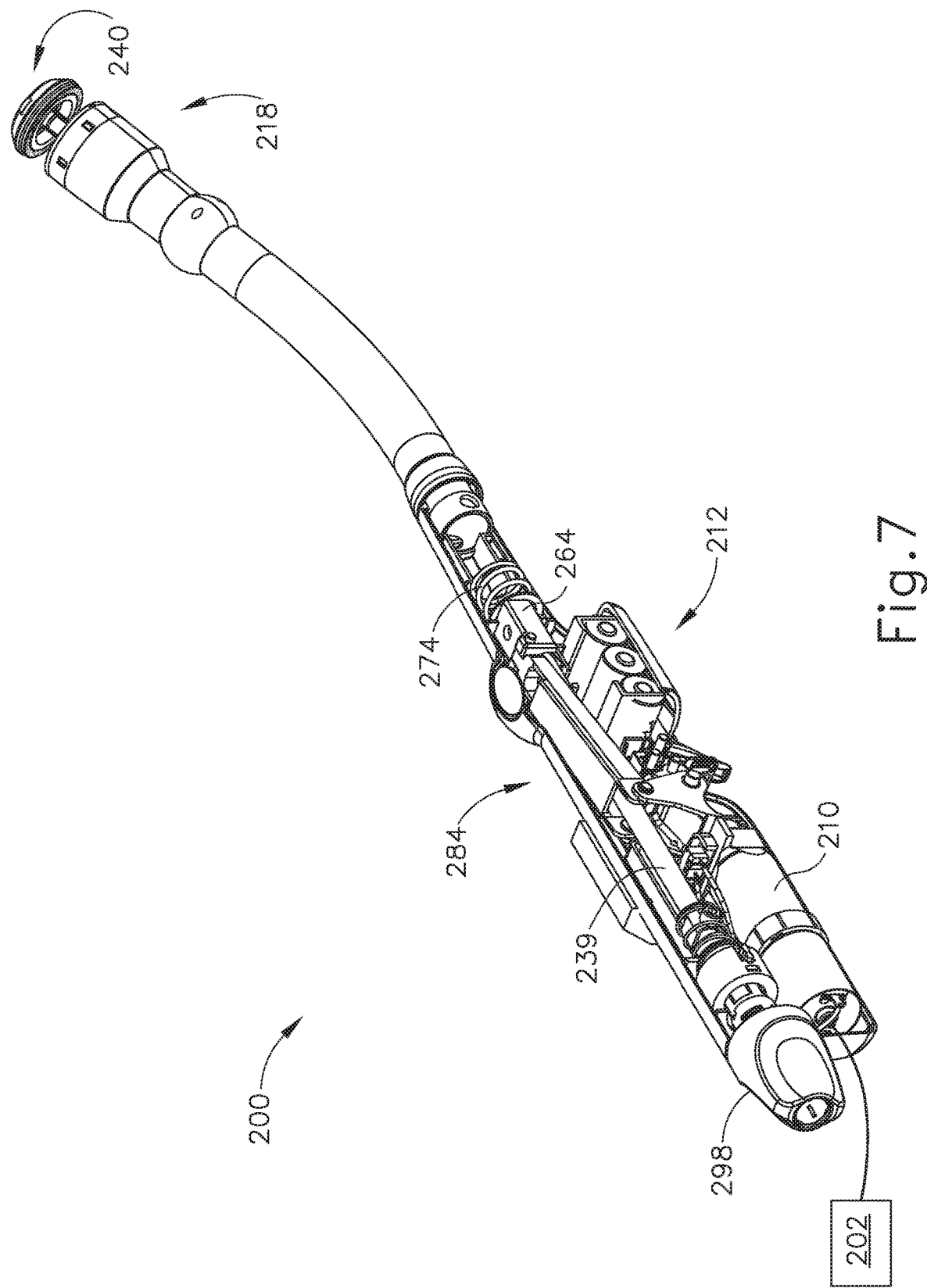

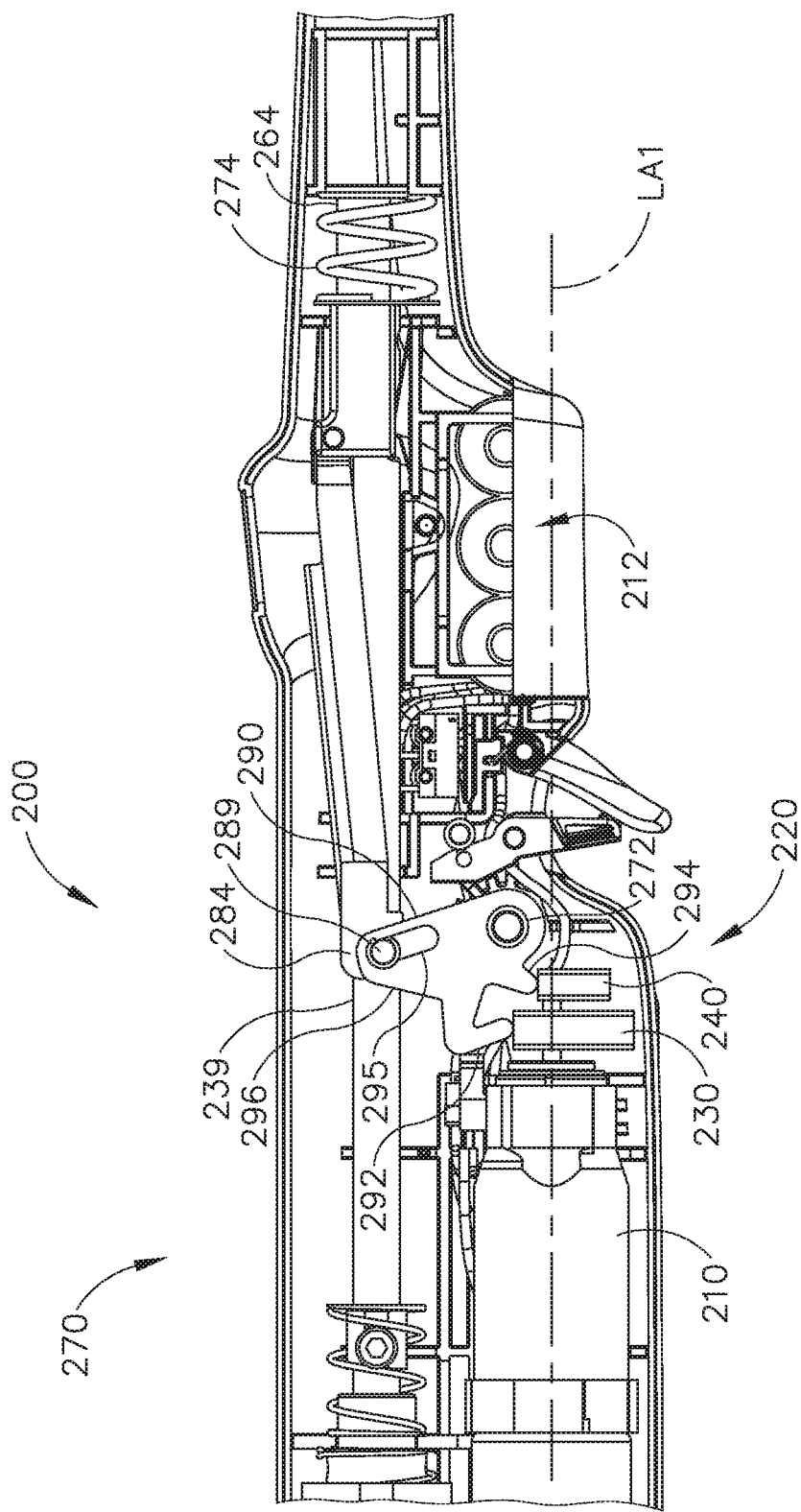

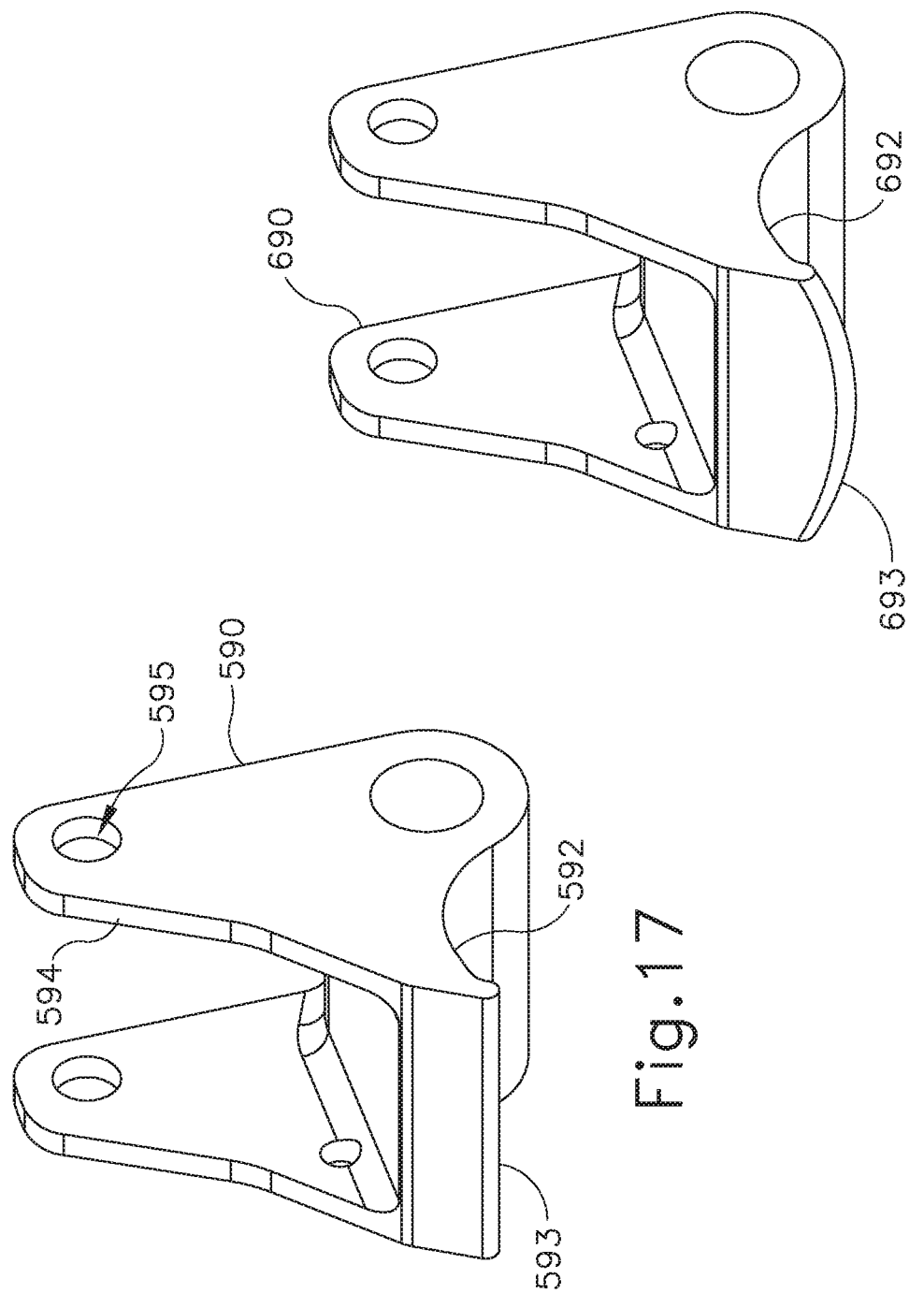

SURGICAL STAPLER WITH ROTARY CAM DRIVE

This application is a Continuation of prior U.S. patent application Ser. No. 14/033,763, entitled "Surgical Stapler With Rotary Cam Drive," filed Sep. 23, 2013, and issued as U.S. Pat. No. 9,713,469 on Jul. 25, 2017.

BACKGROUND

In some settings, a surgeon may want to position a surgical instrument through an orifice of the patient and use the instrument to adjust, position, attach, and/or otherwise interact with tissue within the patient. For instance, in some surgical procedures (e.g., colorectal, bariatric, thoracic, etc.), portions of the gastrointestinal tract and/or esophagus, etc. may be cut and removed to eliminate undesirable tissue or for other reasons. Once the desired tissue is removed, the remaining portions may need to be recoupled together in an end-to-end anastomosis. One such tool for accomplishing these anastomotic procedures is a circular stapler that is inserted through a patient's naturally occurring orifice. Some circular staplers are configured to sever tissue and staple tissue substantially simultaneously. For instance, a circular stapler may sever excess tissue that is interior to an annular array of staples at an anastomosis, to provide a substantially smooth transition between lumen sections that are joined at the anastomosis.

Examples of circular surgical staplers are described in U.S. Pat. No. 5,205,459, entitled "Surgical Anastomosis Stapling Instrument," issued Apr. 27, 1993; U.S. Pat. No. 5,271,544, entitled "Surgical Anastomosis Stapling Instrument," issued Dec. 21, 1993; U.S. Pat. No. 5,275,322, entitled "Surgical Anastomosis Stapling Instrument," issued Jan. 4, 1994; U.S. Pat. No. 5,285,945, entitled "Surgical Anastomosis Stapling Instrument," issued Feb. 15, 1994; U.S. Pat. No. 5,292,053, entitled "Surgical Anastomosis Stapling Instrument," issued Mar. 8, 1994; U.S. Pat. No. 5,333,773, entitled "Surgical Anastomosis Stapling Instrument," issued Aug. 2, 1994; U.S. Pat. No. 5,350,104, entitled "Surgical Anastomosis Stapling Instrument," issued Sep. 27, 1994; and U.S. Pat. No. 5,533,661, entitled "Surgical Anastomosis Stapling Instrument," issued Jul. 9, 1996; and U.S. Pub. No. 2012/0292372, entitled "Low Cost Anvil Assembly for a Circular Stapler," published Nov. 22, 2012, now U.S. Pat. No. 8,910,847, issued on Dec. 16, 2014. The disclosure of each of the above-cited U.S. patents and U.S. patent application Publication is incorporated by reference herein. Some such staplers are operable to clamp down on layers of tissue, cut through the clamped layers of tissue, and drive staples through the layers of tissue to substantially seal the severed layers of tissue together near the severed ends of the tissue layers, thereby joining two severed ends of an anatomical lumen.

Merely additional other exemplary surgical staplers are disclosed in U.S. Pat. No. 4,805,823, entitled "Pocket Configuration for Internal Organ Staplers," issued Feb. 21, 1989; U.S. Pat. No. 5,415,334, entitled "Surgical Stapler and Staple Cartridge," issued May 16, 1995; U.S. Pat. No. 5,465,895, entitled "Surgical Stapler Instrument," issued Nov. 14, 1995; U.S. Pat. No. 5,597,107, entitled "Surgical Stapler Instrument," issued Jan. 28, 1997; U.S. Pat. No. 5,632,432, entitled "Surgical Instrument," issued May 27, 1997; U.S. Pat. No. 5,673,840, entitled "Surgical Instrument," issued Oct. 7, 1997; U.S. Pat. No. 5,704,534, entitled "Articulation Assembly for Surgical Instruments," issued Jan. 6, 1998; U.S. Pat. No. 5,814,055, entitled "Surgical Clamping Mechanism," issued Sep. 29, 1998; U.S. Pat. No. 6,978,921, entitled "Surgical Stapling Instrument Incorporating an E-Beam Firing Mechanism," issued Dec. 27, 2005; U.S. Pat. No. 7,000,818, entitled "Surgical Stapling Instrument Having Separate Distinct Closing and Firing Systems," issued Feb. 21, 2006; U.S. Pat. No. 7,143,923, entitled "Surgical Stapling Instrument Having a Firing Lockout for an Unclosed Anvil," issued Dec. 5, 2006; U.S. Pat. No. 7,303,108, entitled "Surgical Stapling instrument Incorporating a Multi-Stroke Firing Mechanism with a Flexible Rack," issued Dec. 4, 2007; U.S. Pat. No. 7,367,485, entitled "Surgical Stapling Instrument Incorporating a Multistroke Firing Mechanism Having a Rotary Transmission," issued May 6, 2008; U.S. Pat. No. 7,380,695, entitled "Surgical Stapling Instrument Having a Single Lockout Mechanism for Prevention of Firing," issued Jun. 3, 2008; U.S. Pat. No. 7,380,696, entitled "Articulating Surgical Stapling Instrument Incorporating a Two-Piece E-Beam Firing Mechanism," issued Jun. 3, 2008; U.S. Pat. No. 7,404,508, entitled "Surgical Stapling and Cutting Device," issued Jul. 29, 2008; U.S. Pat. No. 7,434,715, entitled "Surgical Stapling Instrument Having Multistroke Firing with Opening Lockout," issued Oct. 14, 2008; and U.S. Pat. No. 7,721,930, entitled "Disposable Cartridge with Adhesive for Use with a Stapling Device," issued May 25, 2010. The disclosure of each of the above-cited U.S. patents is incorporated by reference herein. While the surgical staplers referred to above are described as being used in endoscopic procedures, it should be understood that such surgical staplers may also be used in open procedures and/or other non-endoscopic procedures.

While various kinds of surgical stapling instruments and associated components have been made and used, it is believed that no one prior to the inventor(s) has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 1 depicts a side elevation view of an exemplary circular stapling surgical instrument;

FIG. 2C depicts an enlarged longitudinal cross-sectional view of the stapling head assembly of FIG. 2A showing an exemplary staple driver and blade in a fired position;

FIG. 3 depicts an enlarged partial cross-sectional view of an exemplary staple formed against the anvil;

FIG. 5 depicts an enlarged partial perspective view of an exemplary indicator assembly of the surgical instrument of FIG. 1 showing an indicator window and indicator lever;

FIG. 6 depicts an diagrammatic view of the indicator window of FIG. 5 showing an exemplary indicator bar and exemplary corresponding staple representations;

FIG. 7 depicts a perspective view of an exemplary alternative circular stapling surgical instrument having a motor and exemplary multi-cam assembly;

FIG. 8 depicts a side elevational view of the instrument, motor, and multi-cam assembly of FIG. 7;

FIG. 17 depicts a perspective view of the firing arm of the instrument of FIG. 13;

FIG. 18 depicts a perspective view of an exemplary alternative firing arm that may be incorporated into the instrument of FIG. 13;

Figure 2A:
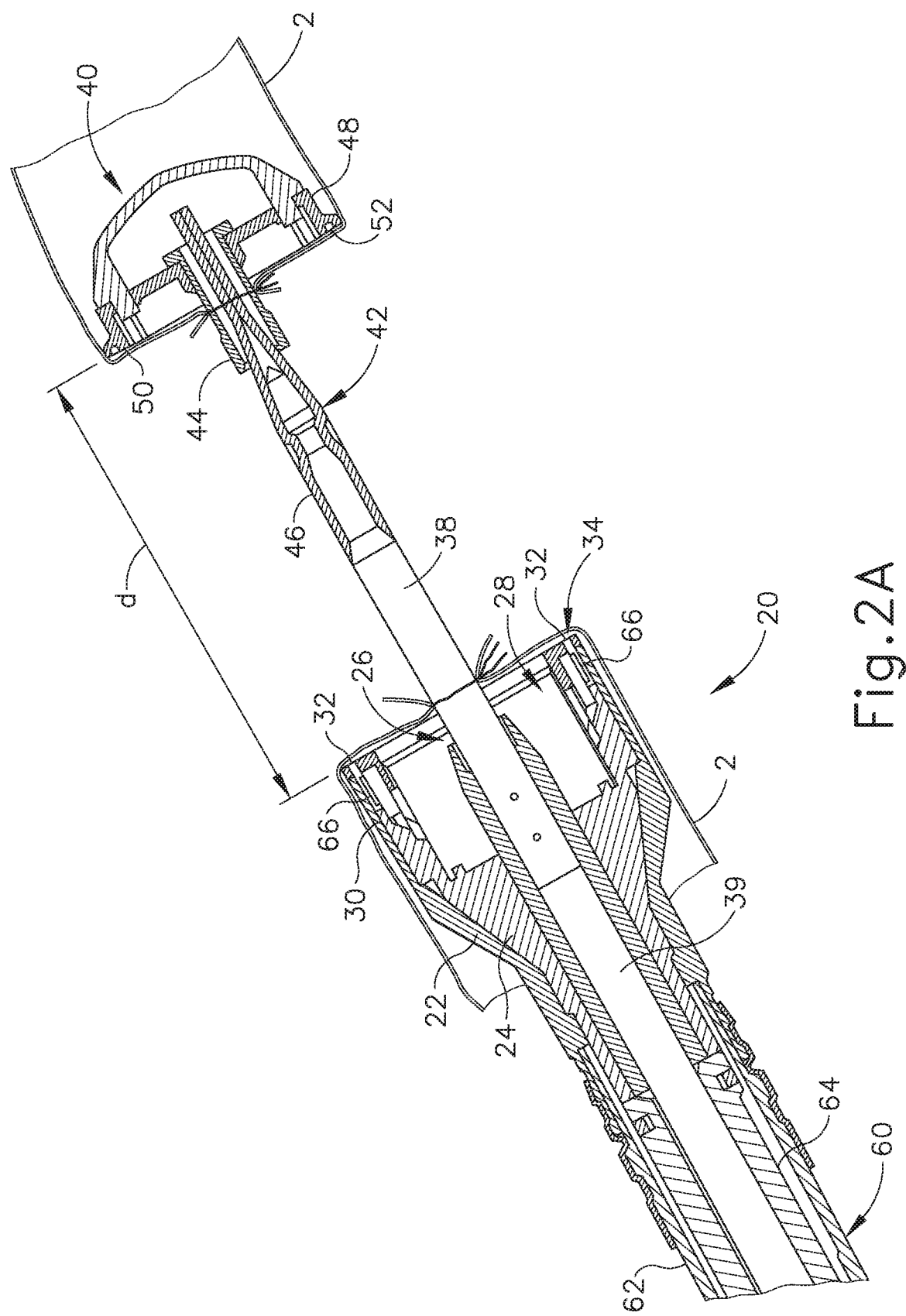
FIG. 2A depicts an enlarged longitudinal cross-section view of an exemplary stapling head assembly of the instrument of FIG. 1 showing an exemplary anvil in an open position.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

I. OVERVIEW OF EXEMPLARY CIRCULAR STAPLING SURGICAL INSTRUMENT

FIGS. 1-6 depict an exemplary circular surgical stapling instrument (10) having a stapling head assembly (20), a shaft assembly (60), and an actuator handle assembly (70), each of which will be described in more detail below. Shaft assembly (60) extends distally from actuator handle assembly (70) and stapling head assembly (20) is coupled to a distal end of shaft assembly (60). In brief, actuator handle assembly (70) is operable to actuate a staple driver (24) of stapling head assembly (20) to drive a plurality of staples (66) out of stapling head assembly (20). Staples (66) are bent to form completed staples by an anvil (40) that is attached at the distal end of instrument (10). Accordingly, tissue (2), shown in FIGS. 2A-2C, may be stapled utilizing instrument (10).

In the present example, instrument (10) comprises a closure system and a firing system. The closure system comprises a trocar (38), a trocar actuator (39), and a rotating knob (98). An anvil (40) may be coupled to a distal end of trocar (38). Rotating knob (98) is operable to longitudinally translate trocar (38) relative to stapling head assembly (20), thereby translating anvil (40) when anvil (40) is coupled to trocar (38), to clamp tissue between anvil (40) and stapling head assembly (20). The firing system comprises a trigger (74), a trigger actuation assembly (84), a driver actuator (64), and a staple driver (24). Staple driver (24) includes a knife (36) configured to sever tissue when staple driver (24) is actuated longitudinally. In addition, staples (66) are positioned distal to a plurality of staple driving features (30) of staple driver (24) such that staple driver (24) also drives staples (66) distally when staple driver (24) is actuated longitudinally. Thus, when trigger (74) is actuated and trigger actuation assembly (84) actuates staple driver (24) via driver actuator (64), knife (36) and members (30) substantially simultaneously sever tissue (2) and drive staples (66) distally relative to stapling head assembly (20)

into tissue. The components and functionalities of the closure system and firing system will now be described in greater detail.

A. Exemplary Anvil

Figure 2B:
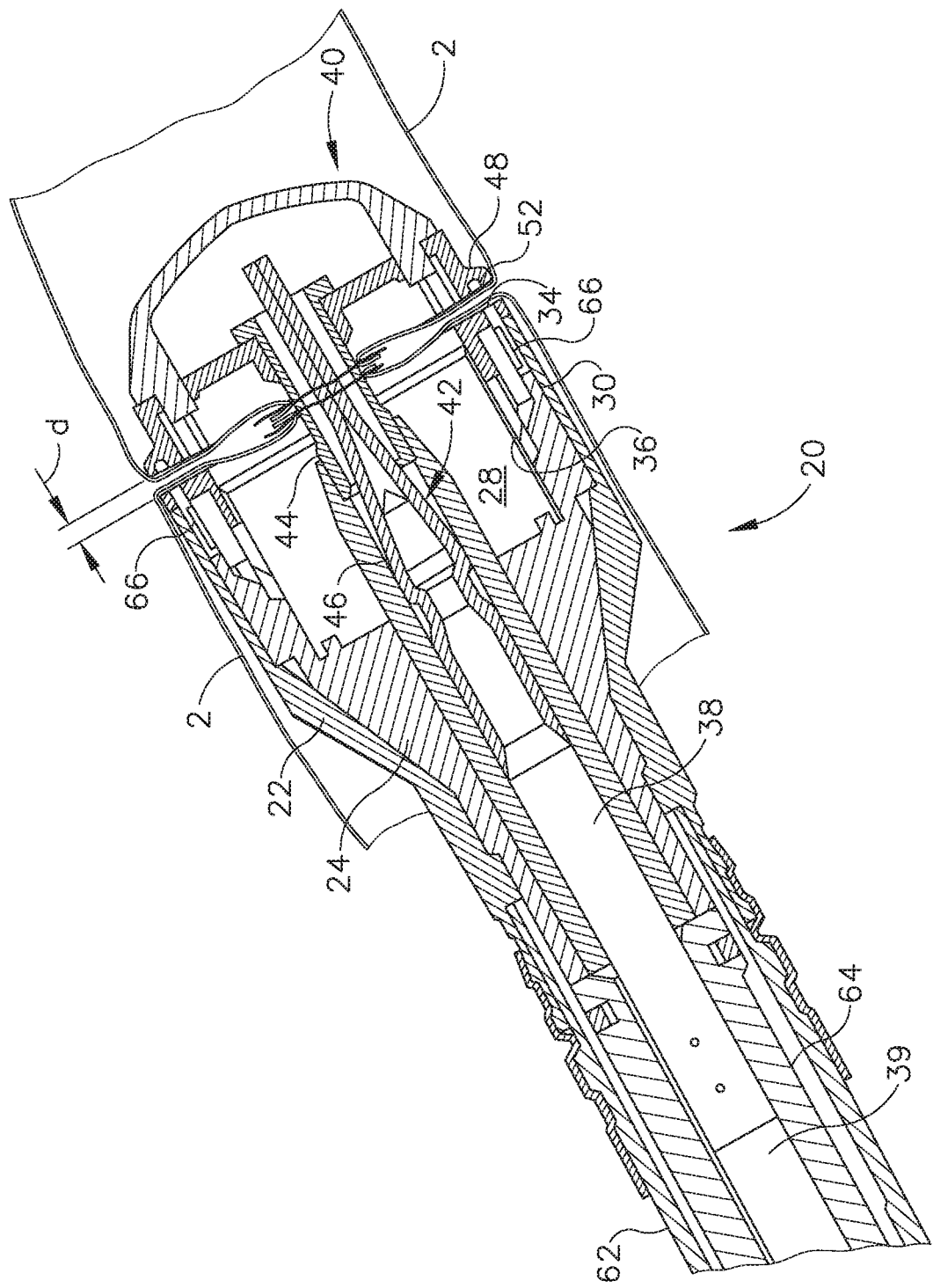
FIG. 2B depicts an enlarged longitudinal cross-sectional view of the stapling head assembly of FIG. 2A showing the anvil in a closed position.

As shown in FIGS. 1-2C, anvil (40) is selectively coupleable to instrument (10) to provide a surface against which staples (66) may be bent to staple material contained between stapling head assembly (20) and anvil (40). Anvil (40) of the present example is selectively coupleable to a trocar or pointed rod (38) that extends distally relative to stapling head assembly (20). Referring to FIGS. 2A-2C, anvil (40) is selectively coupleable via the coupling of a proximal shaft (42) of anvil (40) to a distal tip of trocar (38). Anvil (40) comprises a generally circular anvil head (48) and a proximal shaft (42) extending proximally from anvil head (48). In the example shown, proximal shaft (42) comprises a tubular member (44) having resiliently biased retaining clips (46) to selectively couple anvil (40) to trocar (38), though this is merely optional, and it should be understood that other retention features for coupling anvil (40) to trocar (38) may be used as well. For example, C-clips, clamps, threading, pins, adhesives, etc. may be employed to couple anvil (40) to trocar (38). In addition, while anvil (40) is described as selectively coupleable to trocar (38), in some versions proximal shaft (42) may include a one-way coupling feature such that anvil (40) cannot be removed from trocar (38) once anvil (40) is attached. Merely exemplary one-way features include barbs, one way snaps, collets, collars, tabs, bands, etc. Of course still other configurations for coupling anvil (40) to trocar (38) will be apparent to one of ordinary skill in the art in view of the teachings herein. For instance, trocar (38) may instead be a hollow shaft and proximal shaft (42) may comprise a sharpened rod that is insertable into the hollow shaft.

Anvil head (48) of the present example comprises a plurality of staple forming pockets (52) formed in a proximal face (50) of anvil head (48). Accordingly, when anvil (40) is in the closed position and staples (66) are driven out of stapling head assembly (20) into staple forming pockets (52), as shown in FIG. 2C, legs (68) of staples (66) are bent to form completed staples.

With anvil (40) as a separate component, it should be understood that anvil (40) may be inserted and secured to a portion of tissue (2) prior to being coupled to stapling head assembly (20). By way of example only, anvil (40) may be inserted into and secured to a first tubular portion of tissue (2) while instrument (10) is inserted into and secured to a second tubular portion of tissue (2). For instance, the first tubular portion of tissue (2) may be sutured to or about a portion of anvil (40), and the second tubular portion of tissue (2) may be sutured to or about trocar (38).

As shown in FIG. 2A, anvil (40) is then coupled to trocar (38). Trocar (38) of the present example is shown in a distal most actuated position. Such an extended position for trocar (38) may provide a larger area to which tissue (2) may be coupled prior to attachment of anvil (40). In addition, the extended position of trocar (38) may also provide for easier attachment of anvil (40) to trocar (38). Trocar (38) further includes a tapered distal tip. Such a tip may be capable of piercing through tissue and/or aiding the insertion of anvil (40) on to trocar (38), though the tapered distal tip is merely optional. For instance, in other versions trocar (38) may have a blunt tip. In addition, or in the alternative, trocar (38) may include a magnetic portion (not shown) which may attract anvil (40) towards trocar (38). Of course still further configurations and arrangements for anvil (40) and trocar (38) will be apparent to one of ordinary skill in the art in view of the teachings herein.

When anvil (40) is coupled to trocar (38), the distance between a proximal face of the anvil (40) and a distal face of stapling head assembly (20) defines a gap distance d. Trocar (38) of the present example is translatable longitudinally relative to stapling head assembly (20) via an adjustment knob (98) located at a proximal end of actuator handle assembly (70), as will be described in greater detail below. Accordingly, when anvil (40) is coupled to trocar (38), rotation of adjustment knob (98) enlarges or reduces gap distance d by actuating anvil (40) relative to stapling head assembly (20). For instance, as shown sequentially in FIGS. 2A-2B, anvil (40) is shown actuating proximally relative to actuator handle assembly (70) from an initial, open position to a closed position, thereby reducing the gap distance d and the distance between the two portions of tissue (2) to be joined. Once the gap distance d is brought within a predetermined range, stapling head assembly (20) may be fired, as shown in FIG. 2C, to staple and sever tissue (2) between anvil (40) and stapling head assembly (20). Stapling head assembly (20) is operable to staple and sever tissue (2) by a user pivoting a trigger (74) of actuator handle assembly (70), as will be described in greater detail below.

As noted above, gap distance d corresponds to the distance between anvil (40) and stapling head assembly (20). When instrument (10) is inserted into a patient, this gap distance d may not be easily viewable. Accordingly, a moveable indicator bar (110), shown in FIGS. 5-6, is provided to be visible through an indicator window (120) positioned opposite to trigger (74). Indicator bar (110) is operable to move in response to rotation of adjustment knob (98) such that the position of indicator bar (110) is representative of the gap distance d. As shown in FIG. 6, indicator window (120) further comprises a scale (130) which indicates that the anvil gap is within a desired operating range (e.g., a green colored region or "green zone") and a corresponding staple compression representation at each end of scale (130). By way of example only, as shown in FIG. 6, a first staple image (132) depicts a large staple height while a second staple image (134) depicts a small staple height. Accordingly, a user can view the position of the coupled anvil (40) relative to the stapling head assembly (20) via indicator bar (110) and scale (130). The user may then adjust the positioning of anvil (40) via adjustment knob (98) accordingly.

Referring back to FIGS. 2A-2C, a user sutures a portion of tissue (2) about tubular member (44) such that anvil head (48) is located within a portion of the tissue (2) to be stapled. When tissue (2) is attached to anvil (40), retaining clips (46) and a portion of tubular member (44) protrude out from tissue (2) such that the user may couple anvil (40) to trocar (38). With tissue (2) coupled to trocar (38) and/or another portion of stapling head assembly (20), the user attaches anvil (40) to trocar (38) and actuates anvil (40) proximally towards stapling head assembly (20) to reduce the gap distance d. Once instrument (10) is within the operating range, the user then staples together the ends of tissue (2), thereby forming a substantially contiguous tubular portion of tissue (2).

Anvil (40) may be further constructed in accordance with at least some of the teachings of U.S. Pat. Nos. 5,205,459; 5,271,544; 5,275,322; 5,285,945; 5,292,053; 5,333,773; 5,350,104; 5,533,661; and/or U.S. Pub. No. 2012/0292372, now U.S. Pat. No. 8,910,847, issued on Dec. 16, 2014, the disclosures of which are incorporated by reference herein;

and/or in accordance with other configurations as will be apparent to one of ordinary skill in the art in view of the teachings herein.

B. Exemplary Stapling Head Assembly

Stapling head assembly (20) of the present example is coupled to a distal end of shaft assembly (60) and comprises a tubular casing (22) housing a slidable staple driver (24) and a plurality of staples (66) contained within staple pockets (32). Staples (66) and staple pockets (32) are disposed in a circular array about tubular casing (22). In the present example, staples (66) and staple pockets (32) are disposed in a pair of concentric annular rows of staples (66) and staple pockets (32). Staple driver (24) is operable to actuate longitudinally within tubular casing (22) in response to rotation of trigger (74) of actuator handle assembly (70). As shown in FIGS. 2A-2C, staple driver (24) comprises a flared cylindrical member having a trocar opening (26), a central recess (28), and a plurality of members (30) disposed circumferentially about central recess (28) and extending distally relative to shaft assembly (60). Each member (30) is configured to contact and engage a corresponding staple (66) of the plurality of staples (66) within staple pockets (32). Accordingly, when staple driver (24) is actuated distally relative to actuator handle assembly (70), each member (30) drives a corresponding staple (66) out of its staple pocket (32) through a staple aperture (34) formed in a distal end of tubular casing (22). Because each member (30) extends from staple driver (24), the plurality of staples (66) are driven out of stapling head assembly (20) at substantially the same time. When anvil (40) is in the closed position, staples (66) are driven into staple forming pockets (52) to bend legs (68) of the staples (66), thereby stapling the material located between anvil (40) and stapling head assembly (20). FIG. 3 depicts one merely exemplary staple (66) driven by a member (30) into a staple forming pocket (32) of anvil (40) to bend legs (68).

Staple driver (24) further includes a cylindrical knife (36) that is coaxial to trocar opening (26) and inset from staple pockets (32). In the present example, cylindrical knife (36) is disposed within central recess (28) to translate distally with staple driver (24). When anvil (40) is secured to trocar (38), as described above, anvil head (48) provides a surface against which cylindrical knife (36) cuts the material contained between anvil (40) and stapling head assembly (20). In some versions, anvil head (48) may include a recess (not shown) for cylindrical knife (36) to aid in cutting the material (e.g., by providing a cooperative shearing edge). In addition, or in the alternative, anvil head (48) may include one or more opposing cylindrical knives (not shown) offset from cylindrical knife (36) such that a scissor-type cutting action may be provided. Still other configurations will be apparent to one of ordinary skill in the art in view of the teachings herein. Stapling head assembly (20) is thus operable to both staple and cut tissue (2) substantially simultaneously in response to actuation by actuator handle assembly (70).

Of course stapling head assembly (20) may be further constructed in accordance with at least some of the teachings of U.S. Pat. Nos. 5,205,459; 5,271,544; 5,275,322; 5,285,945; 5,292,053; 5,333,773; 5,350,104; 5,533,661; and/or U.S. Pub. No. 2012/0292372, now U.S. Pat. No. 8,910,847, issued on Dec. 16, 2014, the disclosures of which are incorporated by reference herein; and/or in accordance with other configurations as will be apparent to one of ordinary skill in the art in view of the teachings herein.

As noted previously, staple driver (24) includes a trocar opening (26). Trocar opening (26) is configured to permit trocar (38) to longitudinally slide relative to stapling head assembly (20) and/or shaft assembly (60). As shown in FIGS. 2A-2C, trocar (38) is coupled to a trocar actuator (39) such that trocar (38) can be actuated longitudinally via rotation of rotating knob (98), as will be described in greater detail below in reference to actuator handle assembly (70). In the present example, trocar actuator (39) comprises an elongated, relatively stiff shaft coupled to trocar (38), though this is merely optional. In some versions, actuator (39) may comprise a longitudinally stiff material while permitting lateral bending such that portions of instrument (10) may be selectively bent or curved during use; or instrument (10) may include a preset bent shaft assembly (60). When anvil (40) is coupled to trocar (38), trocar (38) and anvil (40) are translatable via actuator (39) to adjust the gap distance d between anvil (40) and stapling head assembly (20). Still further configurations for actuator (39) to longitudinally actuate trocar (38) will be apparent to one of ordinary skill in the art in view of the teachings herein.

C. Exemplary Shaft Assembly

Stapling head assembly (20) and trocar (38) are positioned at a distal end of shaft assembly (60), as shown in FIGS. 2A-2C. Shaft assembly (60) of the present example comprises an outer tubular member (62) and a driver actuator (64). Outer tubular member (62) is coupled to tubular casing (22) of stapling head assembly (20) and to a body (72) of actuator handle assembly (70), thereby providing a mechanical ground for the actuating components therein. The proximal end of driver actuator (64) is coupled to a trigger actuation assembly (84) of actuator handle assembly (70), described below. The distal end of driver actuator (64) is coupled to staple driver (24) such that the rotation of trigger (74) longitudinally actuates staple driver (24). As shown in FIGS. 2A-2C, driver actuator (64) comprises a tubular member having an open longitudinal axis such that actuator (39) coupled to trocar (38) may actuate longitudinally within and relative to driver actuator (64). Of course it should be understood that other components may be disposed within driver actuator (64) as will be apparent to one of ordinary skill in the art in view of the teachings herein.

Shaft assembly (60) may be further constructed in accordance with at least some of the teachings of U.S. Pat. Nos. 5,205,459; 5,271,544; 5,275,322; 5,285,945; 5,292,053; 5,333,773; 5,350,104; 5,533,661; and/or U.S. Pub. No. 2012/0292372, now U.S. Pat. No. 8,910,847, issued on Dec. 16, 2014, the disclosures of which are incorporated by reference herein; and/or in accordance with other configurations as will be apparent to one of ordinary skill in the art in view of the teachings herein.

D. Exemplary Actuator Handle Assembly

Figure 4A:
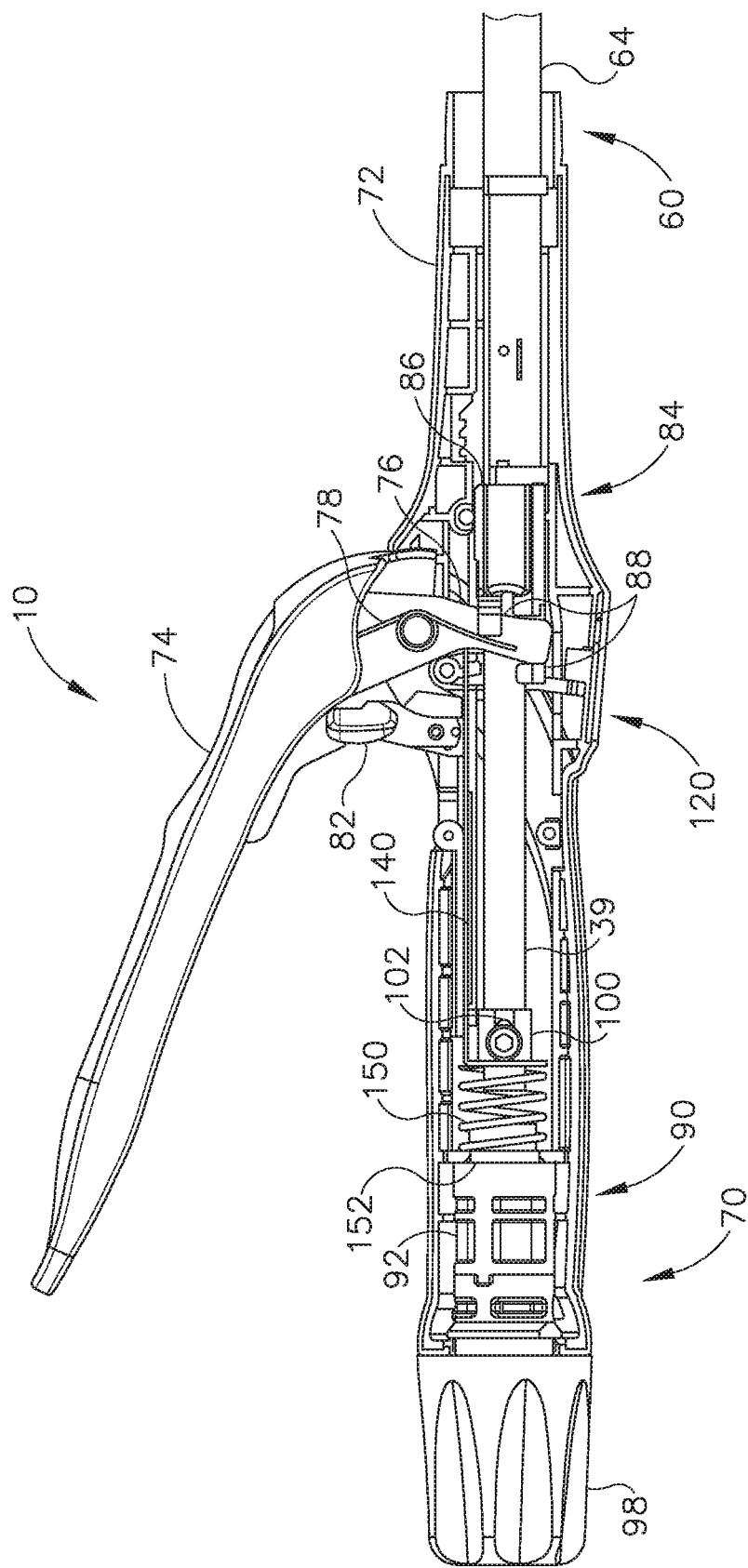
FIG. 4A depicts an enlarged side elevation view of an exemplary actuator handle assembly of the surgical instrument of FIG. 1 with a portion of the body removed, showing a trigger in an unfired position and a lockout feature in a locked position.
Figure 4B:
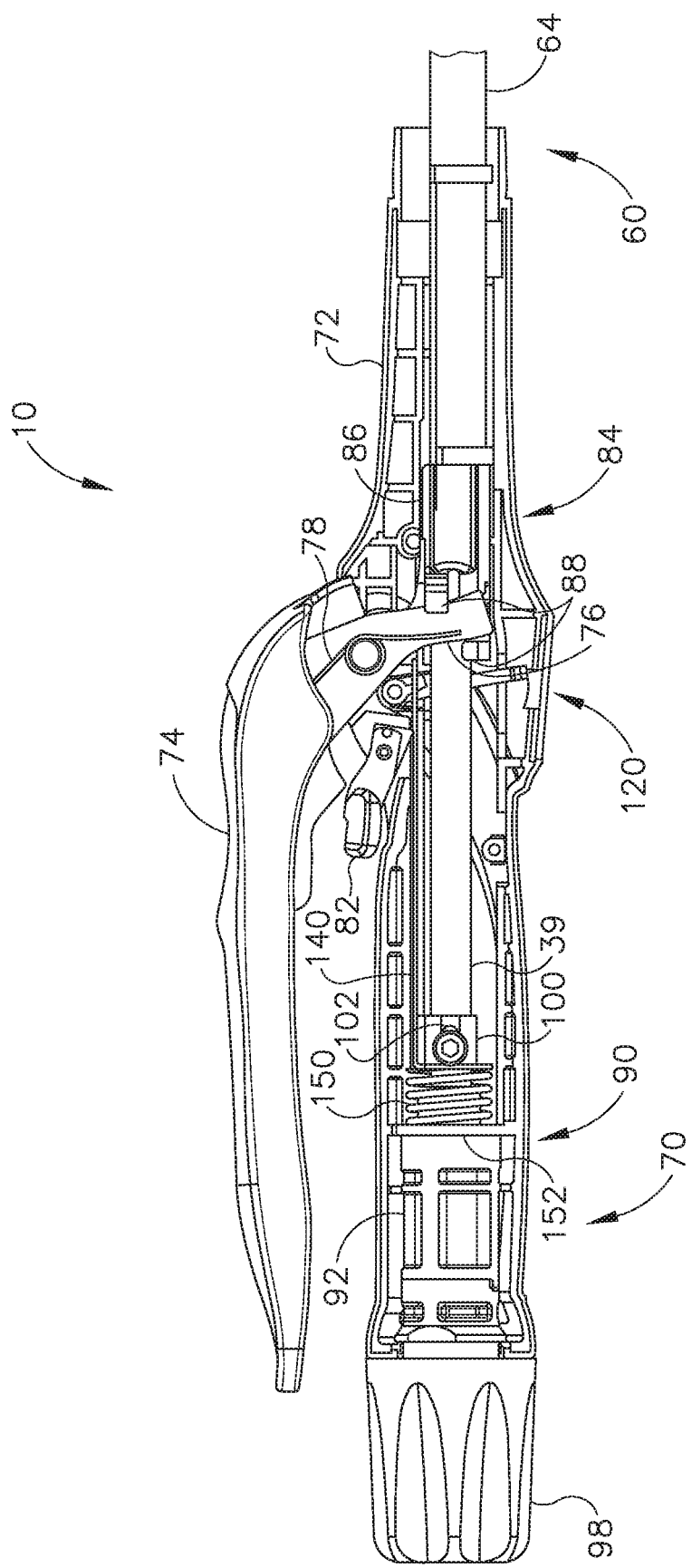
FIG. 4B depicts an enlarged side elevation view of the actuator handle assembly of FIG. 4A, showing the trigger in a fired position and the lockout feature in an unlocked position.

Referring now to FIGS. 4A-5, actuator handle assembly (70) comprises a body (72), a trigger (74), a lockout feature (82), a trigger actuation assembly (84), and a trocar actuation assembly (90). Trigger (74) of the present example is pivotably mounted to body (72) and is coupled to trigger actuation assembly (84) such that rotation of trigger (74) from an unfired position (shown in FIG. 4A) to a fired position (shown in FIG. 4B) actuates driver actuator (64) described above. A spring (78) is coupled to body (72) and trigger (74) to bias trigger (74) towards the unfired position. Lockout feature (82) is a pivotable member that is coupled to body (72). In a first, locked position, lockout feature (82) is pivoted upwards and away from body (72) such that lockout feature (82) engages trigger (74) and mechanically resists actuation of trigger (74) by a user. In a second, unlocked position, such as that shown in FIGS. 1 and 4B, lockout feature (82) is pivoted downward such that trigger

(74) may be actuated by the user. Accordingly, with lockout feature (82) in the second position, trigger (74) can engage a trigger actuation assembly (84) to fire instrument (10).

As shown in FIGS. 4A-4B, trigger actuation assembly (84) of the present example comprises a slidable trigger carriage (86) engaged with a proximal end of driver actuator (64). Carriage (86) includes a set of tabs (88) on a proximal end of carriage (86) to retain and engage a pair of trigger arms (76) extending from trigger (74). Accordingly, when trigger (74) is pivoted, carriage (86) is actuated longitudinally and transfers the longitudinal motion to driver actuator (64). In the example shown, carriage (86) is fixedly coupled to the proximal end of driver actuator (64), though this is merely optional. Indeed, in one merely exemplary alternative, carriage (86) may simply abut driver actuator (64) while a distal spring (not shown) biases driver actuator (64) proximally relative to actuator handle assembly (70).

Trigger actuation assembly (84) may be further constructed in accordance with at least some of the teachings of U.S. Pat. Nos. 5,205,459; 5,271,544; 5,275,322; 5,285,945; 5,292,053; 5,333,773; 5,350,104; 5,533,661; and/or U.S. Pub. No. 2012/0292372, now U.S. Pat. No. 8,910,847, issued on Dec. 16, 2014, the disclosures of which are incorporated by reference herein; and/or in accordance with other configurations as will be apparent to one of ordinary skill in the art in view of the teachings herein.

Body (72) also houses a trocar actuation assembly (90) configured to actuate trocar (38) longitudinally in response to rotation of adjustment knob (98). As best shown in FIGS. 4A-5, trocar actuation assembly (90) of the present example comprises adjustment knob (98), a grooved shank (94), and a sleeve (92). Grooved shank (94) of the present example is located at a proximal end of trocar actuator (39), though it should be understood that grooved shank (94) and trocar actuator (39) may alternatively be separate components that engage to transmit longitudinal movement. While grooved shank (94) is configured to translate within body (72), grooved shank (94) does not rotate within body (72). Adjustment knob (98) is rotatably supported by the proximal end of body (72) and is operable to rotate sleeve (92), which is engaged with grooved shank (94) via an internal tab (not shown). Adjustment knob (98) also defines internal threading (not shown) as will be described in greater detail below. Grooved shank (94) of the present example comprises a continuous groove (96) formed in the outer surface of grooved shank (94). Accordingly, when adjustment knob (98) is rotated, the internal tab of sleeve (92) rides within groove (96) and grooved shank (94) is longitudinally actuated relative to sleeve (92). Since grooved shank (94) is located at the proximal end of trocar actuator (39), rotating adjustment knob (98) in a first direction advances trocar actuator (39) distally relative to actuator handle assembly (70). Accordingly, the gap distance d between anvil (40) and stapling head assembly (20) is increased. By rotating adjustment knob (98) in the opposite direction, trocar actuator (39) is actuated proximally relative to actuator handle assembly (70) to reduce the gap distance d between anvil (40) and stapling head assembly (20). Thus, trocar actuation assembly (90) is operable to actuate trocar (38) in response to rotating adjustment knob (98). Of course other configurations for trocar actuation assembly (90) will be apparent to one of ordinary skill in the art in view of the teachings herein.

Groove (96) of the present example comprises a plurality of different portions (96A, 96B, 96C) that have a varying pitch or number of grooves per axial distance. The present groove (96) is divided into a distal portion (96A), a middle portion (96B) and a proximal portion (96C). As shown in FIG. 5, distal portion (96A) comprises a fine pitch or a high number of grooves over a short axial length of grooved shank (94). Middle portion (96B) comprises a section with comparably coarser pitch or fewer grooves per axial length such that relatively few rotations are required for the internal tab of sleeve (92) to traverse a long axial distance. When anvil (40) is in an initial, distal position in relation to stapling head assembly (20), the internal tab of sleeve (92) is positioned in middle portion (96B). Accordingly, the gap distance d may be quickly reduced through relatively few rotations of adjustment knob (98) while the internal tab of sleeve (92) traverses middle portion (96B). Proximal portion (96C) of the present example is substantially similar to distal portion (96A) and comprises a fine pitch or a high number of grooves over a short axial distance of grooved shank (94) such that a large number of rotations are required to traverse the short axial distance. Proximal portion (96C) of the present example is engaged by the internal threading defined by knob (98) when anvil (40) is substantially near to stapling head assembly (20), such that indicator bar (110) moves within indicator window (120) along scale (130) to indicate that the anvil gap is within a desired operating range, as will be described in more detail below. Accordingly, when grooved shank (94) reaches a proximal position where the proximal portion (96C) of groove (96) engages the internal threading of knob (98), each rotation of adjustment knob (98) may reduce the gap distance d by a relatively small amount to provide for fine tuning. It should be understood that the internal tab of sleeve (92) may be disengaged from groove (96) when proximal portion (96C) is engaged with the internal threading of knob (98).

Trocar actuation assembly (90) may be further constructed in accordance with at least some of the teachings of U.S. Pat. Nos. 5,205,459; 5,271,544; 5,275,322; 5,285,945; 5,292,053; 5,333,773; 5,350,104; 5,533,661, the disclosures of which are incorporated by reference herein; and/or in accordance with other configurations as will be apparent to one of ordinary skill in the art in view of the teachings herein.

In the example shown in FIGS. 4A-4B, a U-shaped clip (100) is attached to an intermediate portion of trocar actuator (39) located distally of grooved shank (94). In the present example, an extension of trocar actuator (39) engages a slot in the housing of handle assembly (70) to prevent trocar actuator (39) from rotating about its axis when adjustment knob (98) is rotated. U-shaped clip (100) of the present example further includes an elongated slot (102) on each of its opposite sides for receiving an attachment member, such as a screw, bolt, pin, etc., to selectively adjust the longitudinal position of elongated slot (102) of U-shaped clip (100) relative to trocar actuator (39) for purposes of calibrating indicator bar (110) relative to scale (130). In some versions, the attachment member (e.g., screw, bolt, pin, etc.) engages with a portion of body (72) to substantially prevent trocar actuator (39) from rotating about its axis when adjustment knob (98) is rotated.

As shown in FIG. 5, actuator handle assembly (70) further includes an indicator bracket (140) configured to engage and pivot an indicator (104). Indicator bracket (140) of the present example is slidable relative to body (72) along a pair of slots formed on body (72). Indicator bracket (140) comprises a rectangular plate (144), an indicator arm (146), and an angled flange (142). Angled flange (142) is formed at the proximal end of rectangular plate (144) and includes an aperture (not shown) to slidable mount onto trocar actuator (39) and/or grooved shank (94). A coil spring (150) is interposed between flange (142) and a boss (152) to bias flange (142) against U-shaped clip (100). Accordingly, when U-shaped clip (100) actuates distally with trocar actuator (39) and/or grooved shank (94), coil spring (150) urges indicator bracket (140) to travel distally with U-shaped clip (100). In addition, U-shaped clip (100) urges indicator bracket (140) proximally relative to boss (152) when trocar actuator (39) and/or grooved shank (94) translate proximally, thereby compressing coil spring (150). Of course, it should be understood that in some versions indicator bracket (140) may be fixedly attached to trocar actuator (39) and/or grooved shank (94).

In the present example, a portion of lockout feature (82) abuts a surface (141) of indicator bracket (140) when indicator bracket (140) is in a longitudinal position that does not correspond to when the anvil gap is within a desired operating range (e.g., a green colored region or "green zone"). When the anvil gap is within a desired operating range (e.g., a green colored region or "green zone"), indicator bracket (140) narrows to provide a pair of gaps (145) on either side of an indicator arm (146) that permits lockout feature (82) to pivot, thereby releasing trigger (74). Accordingly, lockout feature (82) and indicator bracket (140) can substantially prevent a user from releasing and operating trigger (74) until anvil (40) is in a predetermined operating range. Of course it should be understood that lockout feature (82) may be omitted entirely in some versions.

This operating range may be visually communicated to the user via an indicator bar (110) of an indicator (104) shown against a scale (130), described briefly above. At the distal end of indicator bracket (140) is a distally projecting indicator arm (146) which terminates at a laterally projecting finger (148) for controlling the movement of indicator (104). Indicator arm (146) and finger (148), best shown in FIG. 5, are configured to engage a tab (106) of indicator (104) such that indicator (104) is pivoted when indicator bracket (140) is actuated longitudinally. In the present example, indicator (104) is pivotably coupled to body (72) at a first end of indicator (104), though this is merely optional and other pivot points for indicator (104) will be apparent to one of ordinary skill in the art in view of the teachings herein. An indicator bar (110) is positioned on the second end of indicator (104) such that indicator bar (110) moves in response to the actuation of indicator bracket (140). Accordingly, as discussed above, indicator bar (110) is displayed through an indicator window (120) against a scale (130) (shown in FIG. 6) to show the relative gap distance d between anvil (40) and stapling head assembly (20).

Of course indicator bracket (140), indicator (104), and/or actuator handle assembly (70) may be further constructed in accordance with at least some of the teachings of U.S. Pat. Nos. 5,205,459; 5,271,544; 5,275,322; 5,285,945; 5,292,053; 5,333,773; 5,350,104; 5,533,661; and/or U.S. Pub. No. 2012/0292372, now U.S. Pat. No. 8,910,847, issued on Dec. 16, 2014, the disclosures of which are incorporated by reference herein; and/or in accordance with other configurations as will be apparent to one of ordinary skill in the art in view of the teachings herein.

II. EXEMPLARY MOTORIZED CIRCULAR SURGICAL STAPLING INSTRUMENT WITH TRANSLATING CAM FOLLOWER

In some instances, it may be desirable to drive staples (66) and knife (36) in a way that avoids manually driving circular surgical stapling instrument (10). For instance, in the event that the operator has inadequate hand strength to actuate circular surgical stapling instrument (10), it may be desirable to provide a motorized assembly for staple driver (24) and knife (36). Motorizing at least part of instrument (10) may also reduce the risk of operator error in driving staple driver (24) and knife (36). In some cases, operator error with a manually driven instrument (10) may result in instrument (10) failing to actuate fully. This may occur when an operator fails to fully manually actuate trigger (74), which may result in staples (66) not fully forming and thus not fully securing an anastomsis. Thus, motorizing the driving of staple driver (24) and knife (36) may ensure that knife (36) is fully driven to cut tissue, and that staples (66) are fully deployed to fasten tissue, in a single drive stroke. Various examples of how instrument (10) may be reconfigured to incorporate a motor will be described in greater detail below; while other examples will be apparent to those of ordinary skill in the art according to the teachings herein. It should be understood that the examples described below may function substantially similar to instrument (10) described above. In particular, the circular surgical stapling instruments described below may be used to staple tissue in an annular array and sever excess tissue that is interior to the annular array of staples to provide a substantially smooth transition between lumen sections.

While it may be desirable to at least partially motorize circular surgical stapling instrument (10), it may not necessarily be desirable to motorize all portions of circular surgical stapling instrument (10). For instance, it may be desirable to maintain manual adjustment of knob (98) or a similar feature to control the distance d between anvil (40) and stapling head assembly (20). Other suitable portions of circular surgical stapling instrument (10) may also rely on manual actuation despite motorization of other features, as will be apparent to those of ordinary skill in the art in view of the teachings herein.

One merely exemplary variation of a motorized circular surgical stapling instrument (200) is shown in FIG. 7. Instrument (200) of the present example comprises a closure system and a firing system. The closure system of the present example comprises a rotating knob (298), which is operable to drive an anvil (240). Closure system and knob (298) of the present example function substantially similar to the closure system and knob (98) of instrument (10) described above. In particular, knob (298) may be rotated to longitudinally actuate a trocar actuator (239) to enlarge or reduce a gap distance between a proximal face of an anvil (240) and a distal face of a stapling head assembly (218).

The firing system of the present example functions substantially similar to the firing system of instrument (10) described above except for the differences discussed below. In particular, the firing system of the present example may be used to actuate a staple driver and knife (not shown). The firing system of the present example comprises a motor (210), a follower interface feature (284), a driver actuator (264), a staple driver (e.g., like staple driver (24) described above), and a knife (e.g., like knife (36) described above). Driver actuator (264) of the present example is configured to operate substantially similar to driver actuator (64) of instrument (10) discussed above. In particular, a distal end of driver actuator (264) is coupled with the staple driver and knife such that actuation of motor (210) longitudinally translates driver actuator (264), which in turn longitudinally actuates the staple driver and knife. Motor (210) of the present example is powered via a battery pack (212), though it should be understood that motor (210) may be powered by any other appropriate power source including an external power source (e.g. a wall outlet, etc.). As will be discussed in more detail below, motor (210) is operable to actuate stapling head assembly (218). In the present example, motor (210) is oriented along an axis that is parallel to the longitudinal axis defined by driver actuator (264). However, it should be understood that motor (210) may instead be oriented obliquely relative to the longitudinal axis defined by driver actuator (264). By way of example only, a merely illustrative oblique motor orientation is described in greater detail below with reference to FIGS. 22-23.

Stapling head assembly (218) includes the staple driver, a plurality of staples, and the knife, which is configured to sever tissue when the staple driver is actuated longitudinally. Stapling head assembly (218) of the present example functions substantially similar to stapling head assembly (20) described above except for the differences discussed below. In particular, stapling head assembly (218) of the present example may be used to drive an annular array of staples into tissue and to drive the knife to sever excess tissue that is interior to the annular array of staples to provide a substantially smooth transition between lumen sections in response to actuation of the staple driver. A proximal end of driver actuator (264) is coupled with follower interface feature (284) of an actuator handle assembly (270). A distal end of driver actuator (264) is coupled to the staple driver and knife such that longitudinal translation of follower interface feature (284) actuates the staple driver and knife. As will be discussed in more detail below, motor (210) is operable to cause longitudinal translation of follower interface feature (284) via a drive assembly. Thus, when motor (210) is actuated, follower interface feature (284) actuates the staple driver and the knife via driver actuator (264) to substantially simultaneously sever tissue and drive staples distally into the tissue.

As shown in FIG. 7, motor (210) is in communication with an operator input (202). Operator input (202) may include a manually actuated trigger (e.g., similar to trigger (74), etc.) and/or some other input operable to activate motor (210). For instance, operator input (202) could include a button, trigger, lever, slider, touchpad, etc. that electrically activates motor (210). In addition or in the alternative, operator input (202) may include an electrical or software driven actuator operated by the operator to activate motor (210). In some versions, operator input (202) may include a foot actuated pedal in communication with motor (210). Other suitable forms that operator input (202) may take will be apparent to those of ordinary skill in the art in view of the teachings herein.

It will also be understood that operator input (202) may be placed in any appropriate position on or relative to circular surgical stapling instrument (10) as will be apparent to one of ordinary skill in the art in view of the teachings herein. For instance, operator input (202) may be positioned on any portion of actuator handle assembly (70) as seen in FIG. 1. Alternatively, operator input (202) may also be positioned somewhere separately from circular surgical stapling instrument (10), which may include locating operator input (202) on a separate console or computer. Operator input (202) could also be located on a console or device in wireless communication with circular surgical stapling instrument (10). Other suitable locations for operator input (202) will be apparent to those of ordinary skill in the art in view of the teachings herein.

A. First Exemplary Motor and Drive Assembly with Translating Cam Follower

As shown in FIG. 8, motor (210) is disposed within actuator handle assembly (270) parallel to a proximal portion of driver actuator (264). A multi-cam assembly (220) is coupled with a distal end of motor (210). Motor (210) is operable to cause rotation of multi-cam assembly (220) about a longitudinal axis (LA1) defined by motor (210). As best seen in FIGS. 9A-10C, multi-cam assembly (220) comprises a shaft (222) and a pair of cams (230, 240) mounted eccentrically on shaft (222) at different longitudinal positions along longitudinal axis (LA1). In the present example, the housing of handle assembly (270) provides simple support to shaft (222) and the remainder of multi-cam assembly (220). Alternatively, shaft (222) and the remainder of multi-cam assembly (220) may receive support in any other suitable fashion and/or from any other suitable component(s).

Figure 10A:
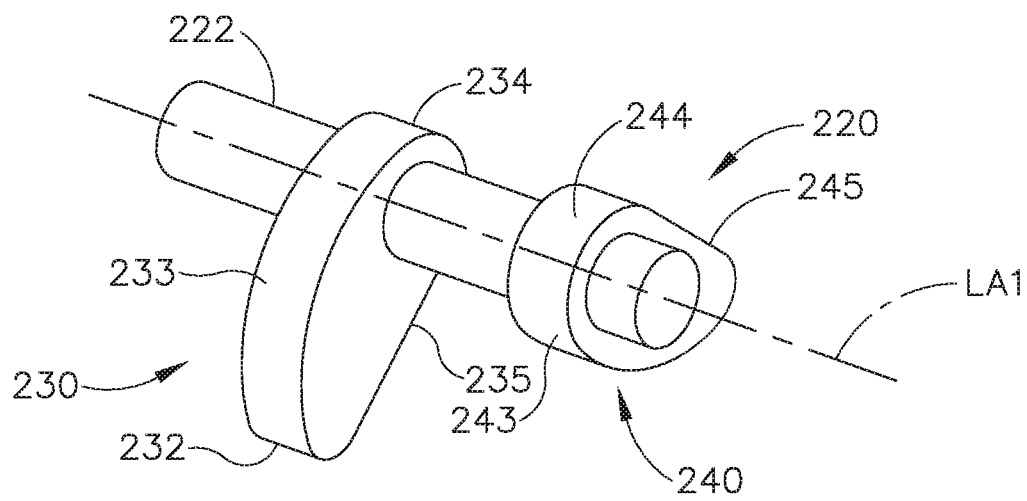
FIG. 10A depicts a perspective view of the multi-cam assembly of FIG. 7 in the first rotational position.
Figure 10B:
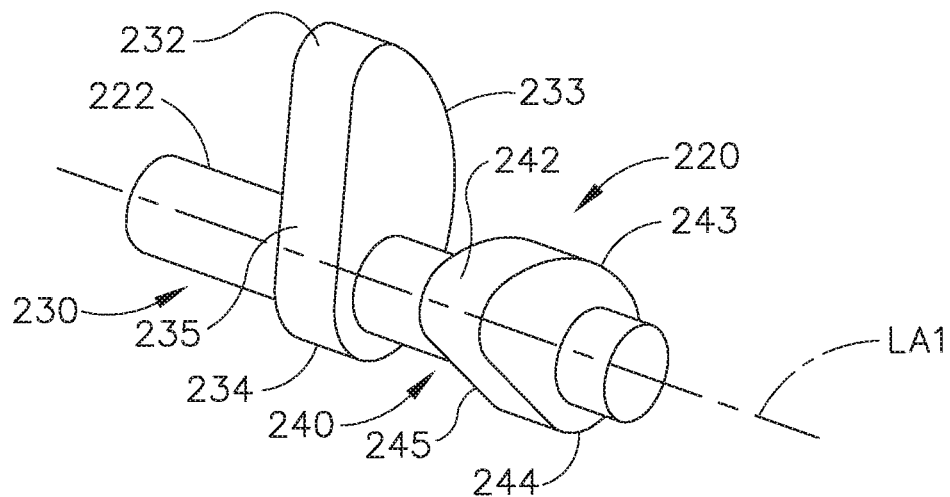
FIG. 10B depicts a perspective view of the multi-cam assembly of FIG. 7 in the second rotational position.
Figure 10C:
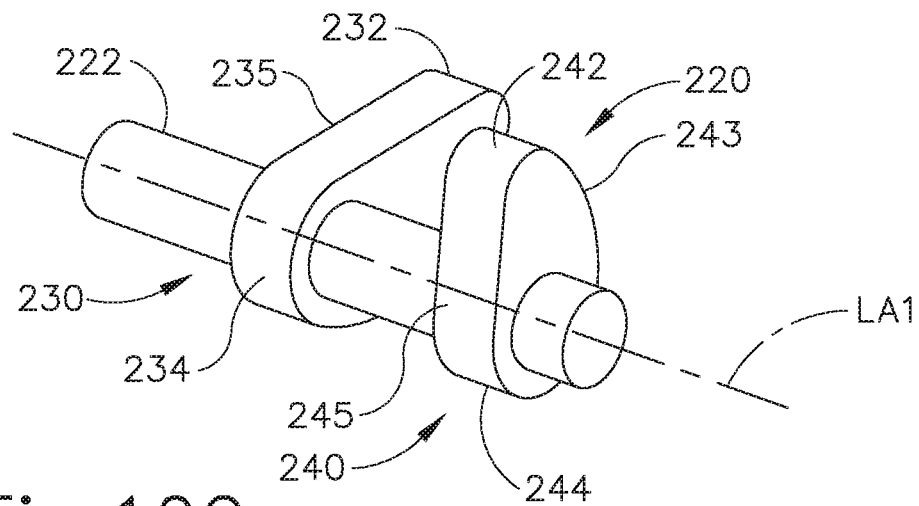
FIG. 10C depicts a perspective view of the multi-cam assembly of FIG. 7 in the third rotational position.

As shown in FIGS. 10A-10C, an exterior surface of first cam (230) comprises a first portion (232) and a second portion (234). First portion (232) and second portion (234) are disposed on radially opposite sides of first cam (230). First portion (232) presents a portion of first cam (230) having a radial distance from longitudinal axis (LA1) that is greater than a radial distance of second portion (234) from longitudinal axis (LA1). First cam (230) further comprises intermediate portions (233, 235) disposed between first portion (232) and second portion (234). Intermediate portions (233, 235) are contoured to provide substantially smooth transition between first portion (232) and second portion (234) along radially opposite sides of first cam (230). Thus, at a particular point along an exterior surface of first cam (230), as first cam (230) is rotated through one revolution, a radial distance from first cam (230) to longitudinal axis (LA1) will change from the greater radial distance presented by first portion (232); to the lesser radial distance presented by second portion (234) via intermediate portion (233); and back to the greater radial distance presented by first portion (232) via intermediate portion (235).

As also shown in FIGS. 10A-10C, an exterior surface of second cam (240) comprises a first portion (242) and a second portion (244). First portion (242) and second portion (244) are disposed on radially opposite sides of second cam (240). First portion (242) presents a portion of second cam (240) having a radial distance from longitudinal axis (LA1) that is greater than a radial distance of second portion (244) from longitudinal axis (LA1). Second cam (240) further comprises intermediate portions (243, 245) disposed between first portion (242) and second portion (244). Intermediate portions (243, 245) are contoured to provide substantially smooth transition between first portion (242) and second portion (244) along radially opposite sides of second cam (240). Thus, at a particular point along an exterior surface of second cam (240), as second cam (240) is rotated through one revolution, a radial distance from second cam (240) to longitudinal axis (LA1) will change from the greater radial distance presented by first portion (242); to the lesser radial distance presented by second portion (244) via intermediate portion (243); and back to the greater radial distance presented by first portion (242) via intermediate portion (245).

Figure 9A:
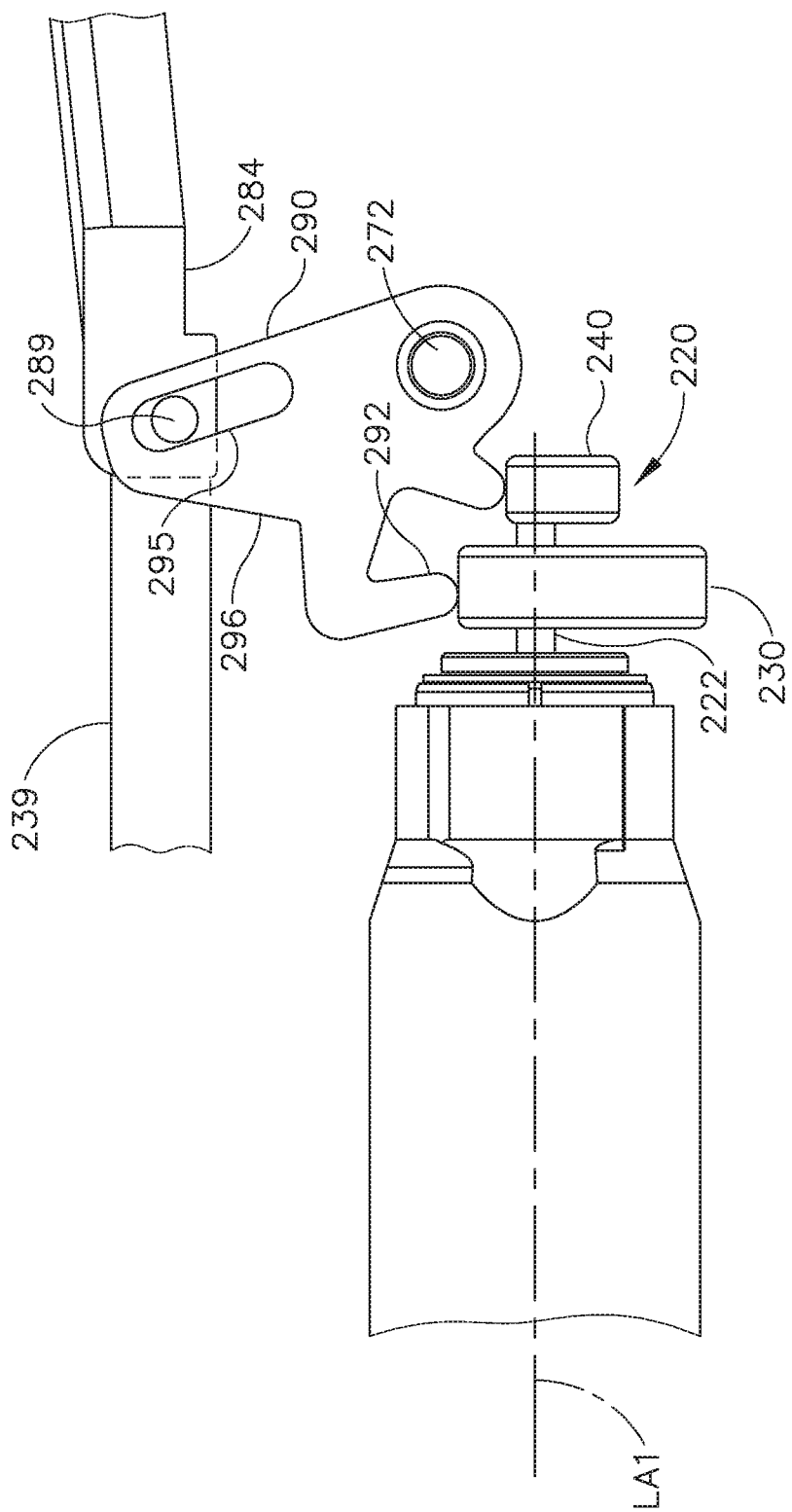
FIG. 9A depicts a side elevational view of the motor and multi-cam assembly of FIG. 7 in a first rotational position.
Figure 9B:
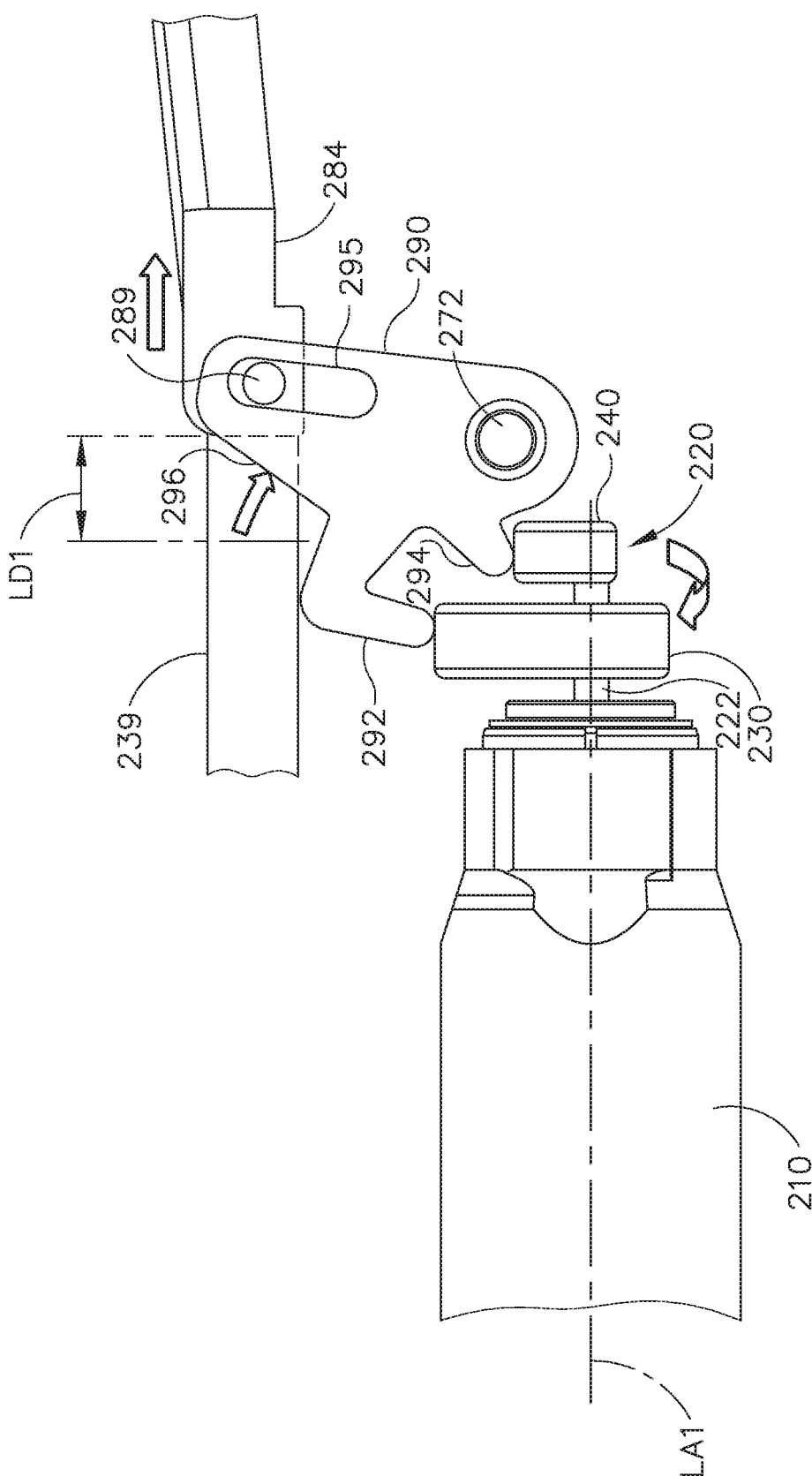
FIG. 9B depicts a side elevational view of the motor and multi-cam assembly of FIG. 7 in a second rotational position.
Figure 9C:
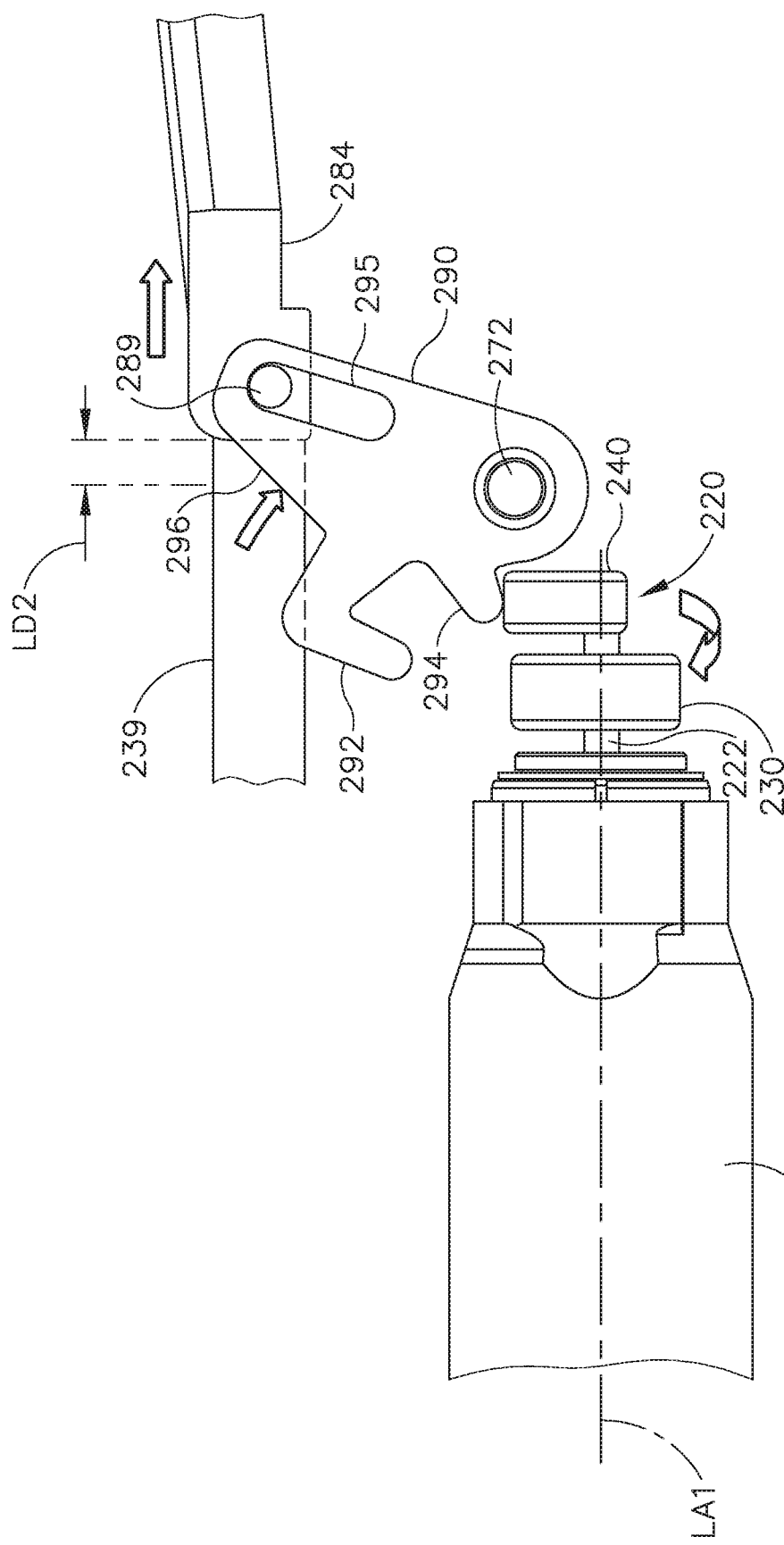
FIG. 9C depicts a side elevational view of the motor and multi-cam assembly of FIG. 7 in a third rotational position.

First cam (230) and second cam (240) are oriented such that first portion (232) of first cam (230) and first portion (242) of second cam (240) are at different angular positions about shaft (222). Further, first cam (230) and second cam (240) are oriented such that second portion (234) of first cam (230) and second portion (244) of second cam (240) are at different angular positions about shaft (222). As best seen in FIGS. 9A-9C, the radial distance of first portion (232) of first cam (230) is greater than that of first portion (242) of second cam (240). The radial distance of second portion (234) of first cam (230) is greater than that of second portion (244) of second cant (240).

As shown in FIG. 9A-9C, follower interface feature (284) is coupled with a pivoting cam follower (290). The handle assembly comprises a pivot pin (272) to which cam follower (290) is rotatably coupled such that cam follower (290) is free to rotate about pivot pin (272). A first arm (292) of cam follower (290) is in contact with first cam (230) at a top of first cam (230) directly vertical of shaft (222) and longitudinal axis (LA1). A second arm (294) of cam follower (290) is in contact with second cam (240) at a top of second cam (240) directly vertical of shaft (222) and longitudinal axis (LA1). A third arm (296) of cam follower (290) presents a slot (295). Follower interface feature (284) comprises a pin (289) extending transversely from follower interface feature (284). Pin (289) is slidably and rotatably disposed within slot (295) such that cam follower (290) is thereby coupled with follower interface feature (284) and further such that, as cam follower (290) rotates about pivot pin (272), follower interface feature (284) translates longitudinally. As shown in FIG. 8, a spring (274) disposed about driver actuator (264) within actuator handle assembly (270) biases follower interface feature (284) longitudinally proximally.

As shown in FIGS. 9A and 10A, with multi-cam assembly (220) in a first rotational position, second portion (234) of first cam (230) is positioned above longitudinal axis (LA1). In this first rotational position, first arm (292) of cam follower (290) is in contact with second portion (234) of first cam (230). Second portion (244) of second cam (240) is positioned toward longitudinal axis (LA1). However, second arm (294) of cam follower (290) is not in contact with the exterior surface of second cam (240). With multi-cam assembly (220) in this first rotational position, follower interface feature (284) is in a proximal longitudinal position.

As shown in FIGS. 9B and 10B, multi-cam assembly (220) is rotated approximately 135° to a second rotational position. In this second rotational position, first cam (230) has been rotated such that first portion (232) of first cam (230) is positioned above longitudinal axis (LA1) and such that first arm (292) of cam follower (290) is now in contact with first portion (232) of first cam (230). It should be understood that, as first cam (230) is rotated from the first rotational position to the second rotational position, first arm (292) of cam follower (290) is driven from the lesser radial distance presented by second portion (234) to the greater radial distance presented by first portion (232) via intermediate portion (233), thus rotating cam follower (290) about pivot pin (272). Further, as cam follower (290) rotates about pivot pin (272), third arm (296) is also rotated, and follower interface feature (284) is driven longitudinally distally a first longitudinal distance (LD1) against the proximal bias of spring (274) by rotation of third arm (296). Also in this second rotational position, second cam (240) has been rotated such that intermediate portion (243) of second cam (240) is positioned at the top of second cam (240) and such that second arm (294) of cam follower (290) is now in contact with intermediate portion (243) of second cam (240) in the second rotational position.

As shown in FIGS. 9C and 10C, multi-cam assembly (220) is rotated approximately a further 45° to a third rotational position. In this third rotational position, second cam (240) has been rotated such that first portion (242) of second cam (240) is positioned above longitudinal axis (LA1) and such that second arm (294) of cam follower (290) is now in contact with first portion (242) of second cam (240). It should therefore be understood that as second cam (240) is rotated from the first rotational position to the second rotational position, and then to the third rotational position, second arm (294) of cam follower (290) is driven from the lesser radial distance caused by contact between first arm (292) and second portion (234) of first cam (230) to the greater radial distance presented by first portion (242) of second cam (240) via intermediate portion (243), thus further rotating cam follower (290) about pivot pin (272). As cam follower (290) further rotates about pivot pin (272), third arm (296) is also rotated further, and follower interface feature (284) is driven longitudinally distally a second longitudinal distance (LD2) against the proximal bias of spring (274) into a distal longitudinal position. Also in this third rotational position, first cam (230) has been rotated such that intermediate portion (235) of first cam (230) is positioned above longitudinal axis (LA1) and such that first arm (292) of cam follower (290) is no longer in contact with first cam (230).

Further rotation of multi-cam assembly (220) will transition multi-cam assembly (220) back into the first rotational position after multi-cam assembly (220) completes a full 360° of rotation, thus allowing follower interface feature (284) to be driven back into the proximal longitudinal position. Follower interface feature (284) may be driven proximally by spring (274) as rotated cams (230, 240) provide clearance for such proximal movement. It should be understood that proximal movement of follower interface feature (284) will cause cam follower (290) to remain in contact with multi-earn assembly (220). Translation of follower interface feature (284) from the proximal longitudinal position to the distal longitudinal position and back to the proximal longitudinal position will cause the staple driver to be driven from a proximal position to a distal position and back again via driver actuator (264). The distal motion of driver actuator (264) will deploy staples at the anastomosis site and sever excess tissue within the anastomosis; while the subsequent proximal motion of driver actuator will facilitate removal of stapling head assembly (218) and anvil (240) from the anastomosis site.

It should be understood that longitudinal distances (LD1, LD2) may be manipulated by manipulating the radial distances represented by portions (232, 234, 242, 244) of earns (230, 240) and/or arms (292, 294, 296). For instance, in the present example, first longitudinal distance (LD1) is greater than the second longitudinal distance (LD2). Different longitudinal distances (LD1, LD2) may impart a mechanical advantage to driver actuator (264) that varies through the full range of distal motion of driver actuator (264). This varying mechanical advantage may facilitate breakage of a washer as will be described in greater detail below; and/or may provide other results as will be apparent to those of ordinary skill in the art in view of the teachings herein.

Intermediate portions (233, 243) and intermediate portions (234, 245) may have different contours. These different contours may represent different rates of change of the radial distance from the exterior surfaces of cams (230, 240) to longitudinal axis (LA1) presented by first portions (232, 242) to second portions (234, 244) and vice versa. In particular, intermediate portions (233, 243) may represent a more gradual rate of change from the radial distance presented by second portions (234, 244) to the radial distance presented by first portions (232, 242) whereas intermediate portions (235, 245) may represent a more rapid rate of change from the radial distance presented by first portions (232, 242) to the radial distance presented by second portions (234, 244) or vice versa depending upon which direction in which cams (230, 240) are rotated. These differing rates of change will be communicated to follower interface feature (284), driver actuator (264), and the staple driver via cam follower (290), thus causing differing rates of longitudinal translation of follower interface feature (284), driver actuator (264), and the staple driver. For instance, intermediate portions (233, 243) may provide a relatively slow rate of distal advancement of driver actuator (264) while intermediate portion (235, 245) provides a relatively rapid rate of proximal retraction of driver actuator (264). Of course, these rates may be further varied in any suitable way.

Figure 24:
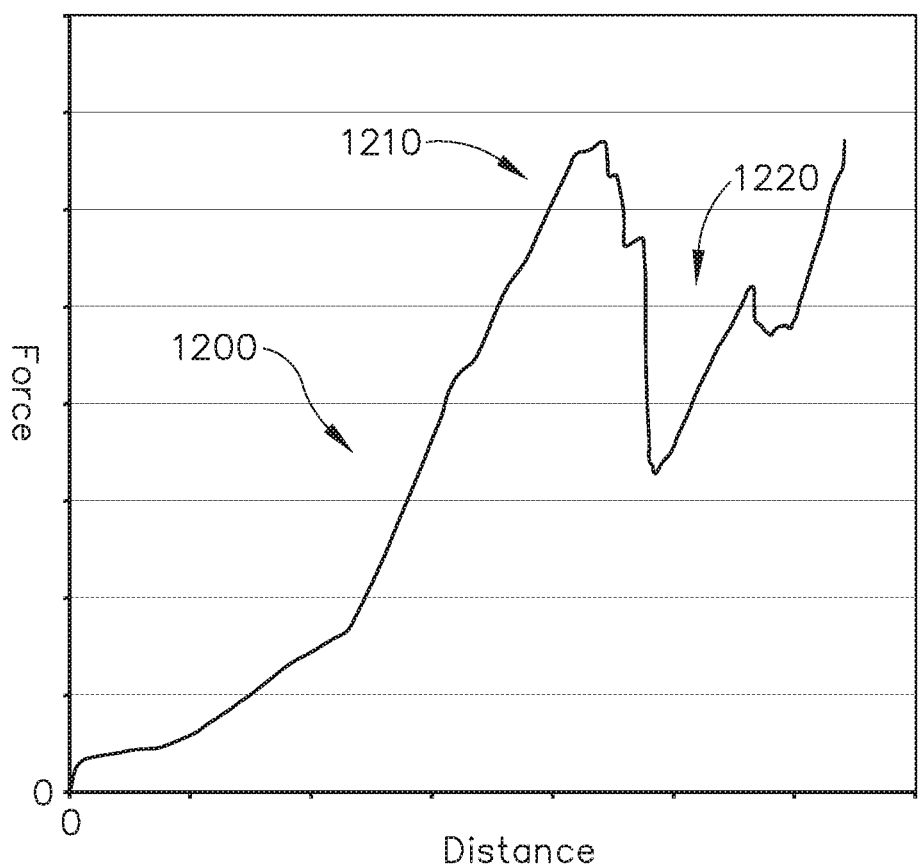
FIG. 24 depicts an exemplary force profile associated with a firing stroke for a circular stapling surgical instrument.

In some versions of instrument (200), anvil (240) contains a breakable washer that is broken by the knife when the knife completes a full distal range of motion. In some instances, the washer thus provides an audible or haptic feedback through actuator handle assembly (270) as the washer breaks in response to completion of full advancement of the knife toward anvil (240), though such audible/haptic feedback is not necessary. It should be understood that the presence of the washer may present a sudden increase in the force required to advance driver actuator (264) distally. FIG. 24 shows an exemplary force profile encountered by driver actuator (264) during the range of distal travel of driver actuator (264). In a first range (1200) of distal motion, driver actuator (264) encounters a gradually increasing load or resisting force as the knife passes through tissue. In a second range (1210) of distal motion, driver actuator (264) encounters a spike in load or resisting force as the knife passes through the washer. In a third range (1220) of distal motion, driver actuator (264) first encounters a sudden drop in load or resisting force after the washer breaks, then a subsequent increase in load or resisting force as stapling head assembly (218) drives staples into anvil (240) to thereby form staples to their final height. In view of the foregoing, it should be further understood that during the transition from the position shown in FIG. 9A to the position shown in FIG. 9C, the radial distances represented by portions (232, 234, 242, 244) of cams (230, 240) and/or arms (292, 294, 296) may provide an increasing mechanical advantage as driver actuator (264) reaches the end of its distal movement, thereby providing greater force by which to break the washer and form the staples. For instance, the knife may encounter the washer as the knife travels through the second longitudinal distance (LD2), and the mechanical advantage provided during movement through the second longitudinal distance (LD2) may be greater than the mechanical advantage provided during movement through the first longitudinal distance (LD1) in order to account for increased mechanical resistance provided by the washer forming the staples. Of course, in some versions, the breakable washer may be omitted entirely in some versions.

B. Second Exemplary Motor and Drive Assembly with Translating Cam Follower

Figure 11A:
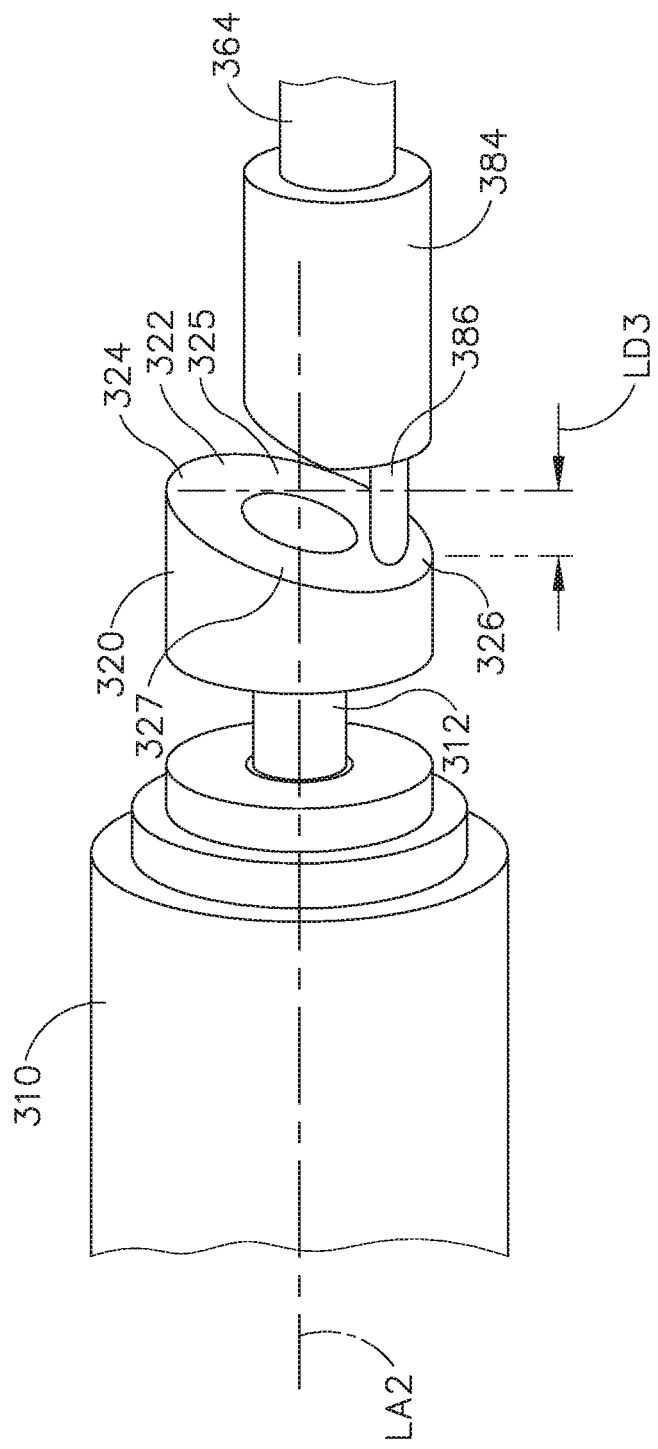
FIG. 11A depicts a side elevational view of an exemplary motor and sloped cam that may be incorporated into the instrument of FIG. 7, in a first rotational position.
Figure 11B:
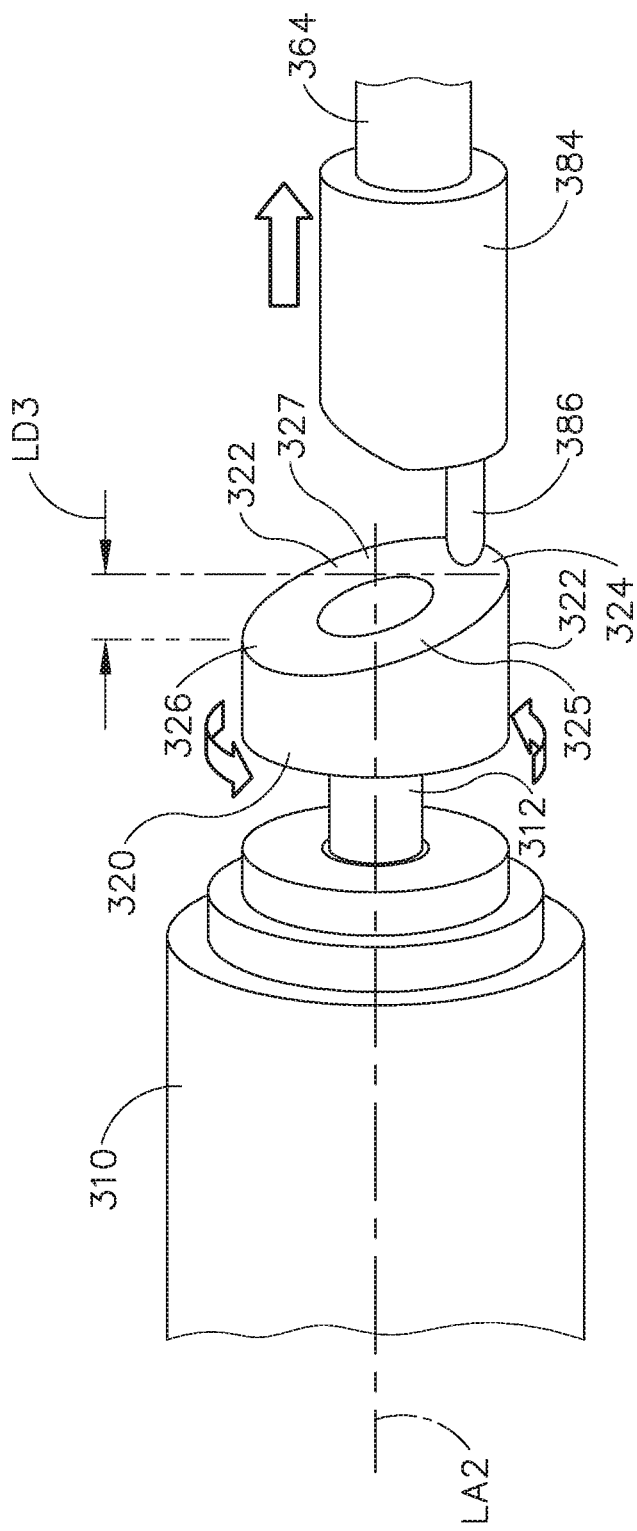
FIG. 11B depicts a side elevational view of the motor and sloped cam of FIG. 11A in a second rotational position.

As a variation of instrument (200) discussed above, instrument (200) may be provided with a motor coaxially aligned with driver actuator (264). Such an arrangement is depicted in FIGS. 11A-11B, which shows exemplary alternative components that may be incorporated into instrument (200) to actuate the staple driver and knife. In particular, FIGS. 11A-11B show an exemplary alternative motor (310) and barrel cam (320) configured to operate substantially similar to motor (210) and barrel cam (220) discussed above except for the differences discussed below. Motor (310), barrel cam (320), and a spring (not shown) are configured to drive a stapling head assembly (not shown) distally and proximally through one revolution of barrel cam (320) via translation of a driver actuator (364) and a cam follower (384). Cam follower (384) is coupled to driver actuator (364). Driver actuator (364) of the present example is configured to operate substantially similar to driver actuator (64) of instrument (10) discussed above. In particular, a distal end of driver actuator (364) is coupled to the stapling head assembly such that driver actuator (364) actuates the stapling head assembly when motor (310) longitudinally translates driver actuator (364).

As shown in FIGS. 11A-11B, motor (310) is disposed within an actuator handle assembly (not shown) such that motor (310) is coaxially aligned with driver actuator (364). In some other versions, motor (310) is oriented obliquely relative to the longitudinal axis defined by driver actuator (364). By way of example only, a merely illustrative oblique motor orientation is described in greater detail below with reference to FIGS. 22-23. In the present example, a barrel cam (320) is coupled with a distal end of motor (310) via a shaft (3112). Motor (310) is operable to rotate barrel cam (320) about a longitudinal axis (LA2) defined by motor (310). As shown in FIG. 11A, barrel cam (320) comprises a sloped distal cam face (322). Sloped cam face (322) comprises a distal portion (324) and a proximal portion (326). Distal portion (324) and proximal portion (326) are disposed on radially opposite sides of barrel cam (320). Distal portion (324) presents a portion of sloped cam face (322) having a longitudinal position relative to longitudinal axis (LA2) more distal than that of proximal portion (326), thus defining a longitudinal distance (LD3) between distal portion (324) and proximal portion (326). Sloped cam face (322) further comprises intermediate portions (325, 327) disposed between distal portion (324) and proximal portion (326). Intermediate portions (325, 327) are contoured to provide substantially smooth transition between distal portion (324) and proximal portion (326) along opposite sides of barrel cam (320). Thus, at a particular point along sloped cam face (322) as barrel cam (320) is rotated through one revolution, a longitudinal position of sloped cam face (322) will change from the proximal position presented by proximal portion (326) to the distal position presented by distal portion (324) and back again.

As shown in FIGS. 11A-11B, cam follower (384) comprises a contact prong (386) extending proximally from cam follower (384). Contact prong (386) is secured to cam follower (384) such that longitudinal translation of contact prong (386) causes longitudinal translation of cam follower (384). A proximal end of contact prong (386) is in contact with sloped cam face (322). Contact prong (386) is configured to remain in contact with sloped cam face (322) as barrel cam (320) rotates. For instance, a spring (not shown) may be coaxially positioned about driver actuator (364) within the actuator handle assembly in order to bias cam follower (384) proximally such that contact prong (386) remains in contact with sloped cam face (322). Thus, as barrel cam (320) is rotated through one revolution, a longitudinal position of cam follower (384) will translate from a proximal position caused by contact between the proximal end of contact prong (386) and proximal portion (326) of sloped cam face (322) to a distal position caused by contact between the proximal end of contact prong (386) and distal portion (324) of sloped cam face (322); and back again to the proximal position caused by the resilient bias of the spring.

FIG. 11A shows a configuration where contact prong (386) is in a proximal longitudinal position, in contact with proximal portion (326) of sloped cam face (322) of barrel cam (320). In this position, cam follower (384) is in the proximal position, and thus the staple driver remains in a proximal position. As shown in FIG. 11B, as motor (310) rotates barrel cam (320) 180°, contact prong (386) remains in contact with sloped cam face (322) because of the proximal bias of the spring. During this rotation, contact prong (386) is transitioned via intermediate portion (325) from proximal portion (326) to distal portion (324), and thus cam follower (384) is driven distally the distance of longitudinal distance (LD3) to a distal longitudinal position against the proximal bias of the spring. As motor (310) further rotates barrel cam (320) a complete 360°, contact prong (386) remains in contact with sloped cam face (322) because of the proximal bias of the spring. During this rotation, contact prong (386) is transitioned via intermediate portion (327) from distal portion (324) to proximal portion (326), such that the spring drives cam follower (384) proximally the distance of longitudinal distance (LD3) into the proximal longitudinal position. Translation of cam follower (384) from the proximal longitudinal position to the distal longitudinal position and back to the proximal longitudinal position will cause the staple driver to be driven from a proximal position to a distal position and back again via driver actuator (364).

Figure 12:
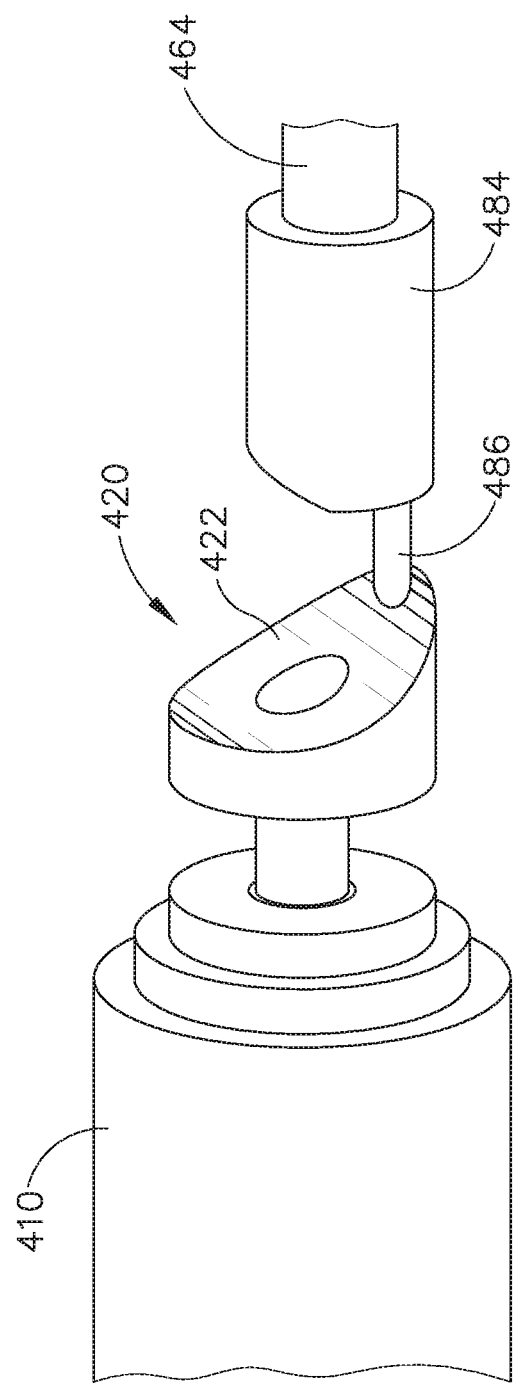
FIG. 12 depicts a perspective view of an exemplary alternative sloped cam that may be incorporated into the instrument of FIG. 7.

In some versions, it may be desirable to vary the mechanical advantage imparted to cam follower (384) along longitudinal distance (LD3) through the range of angular travel by barrel cam (420). One merely exemplary variation of a barrel cam (420) is shown in FIG. 12. Barrel cam (420) is driven by a motor (410). Barrel cam (420) comprises a variable sloped face (422) configured to operate substantially similar to barrel cam (320). In particular, barrel cam (420) and a spring (not shown) are configured to drive a staple driver (not shown) distally and proximally through one revolution of barrel cam (420) via translation of a driver actuator (464) and a cam follower (484). Variable sloped face (422) presents a series of arcuate slopes with having differing slopes and contours which represent a series of varying advantages imparted to cam follower (484). Cam follower (484) comprises a contact prong (486). Contact prong (486) is secured to cam follower (484) such that longitudinal translation of contact prong (486) causes longitudinal translation of cam follower (484).

A proximal end of contact prong (486) is in contact with variable sloped face (422). Contact prong (486) is configured to remain in contact with sloped face (422) as variable barrel cam (420) rotates because of proximal bias exerted by the spring upon cam follower (484). Thus, as barrel cam (420) rotates through an entire revolution, cam follower (484) is driven longitudinally with varying mechanical advantage through the series of varying translation rates from a proximal position to a distal position and back to the proximal position. This varying longitudinal translation of cam follower (484) from the proximal longitudinal position to the distal longitudinal position and back to the proximal longitudinal position will cause the staple driver to be driven from a proximal position to a distal position and back again via driver actuator (464). In the present example, motor (410) is oriented along an axis that is parallel to the longitudinal axis defined by driver actuator (464). However, it should be understood that motor (210) may instead be oriented obliquely relative to the longitudinal axis defined by driver actuator (264). By way of example only, a merely illustrative oblique motor orientation is described in greater detail below with reference to FIGS. 22-23.

Some versions of instrument (400) contain a breakable washer that is broken by the knife when the knife completes a full distal range of motion, as discussed above with reference to FIG. 24. It will further be understood that the arcuate slopes of variable sloped face (422) may provide an increasing mechanical advantage as the knife reaches the end of its distal movement, thereby providing greater force by which to break the washer. Again, though, the breakable washer may be omitted entirely in some versions.

III. EXEMPLARY MOTORIZED SURGICAL STAPLING INSTRUMENT WITH PIVOTING CAM FOLLOWER

Figure 13:
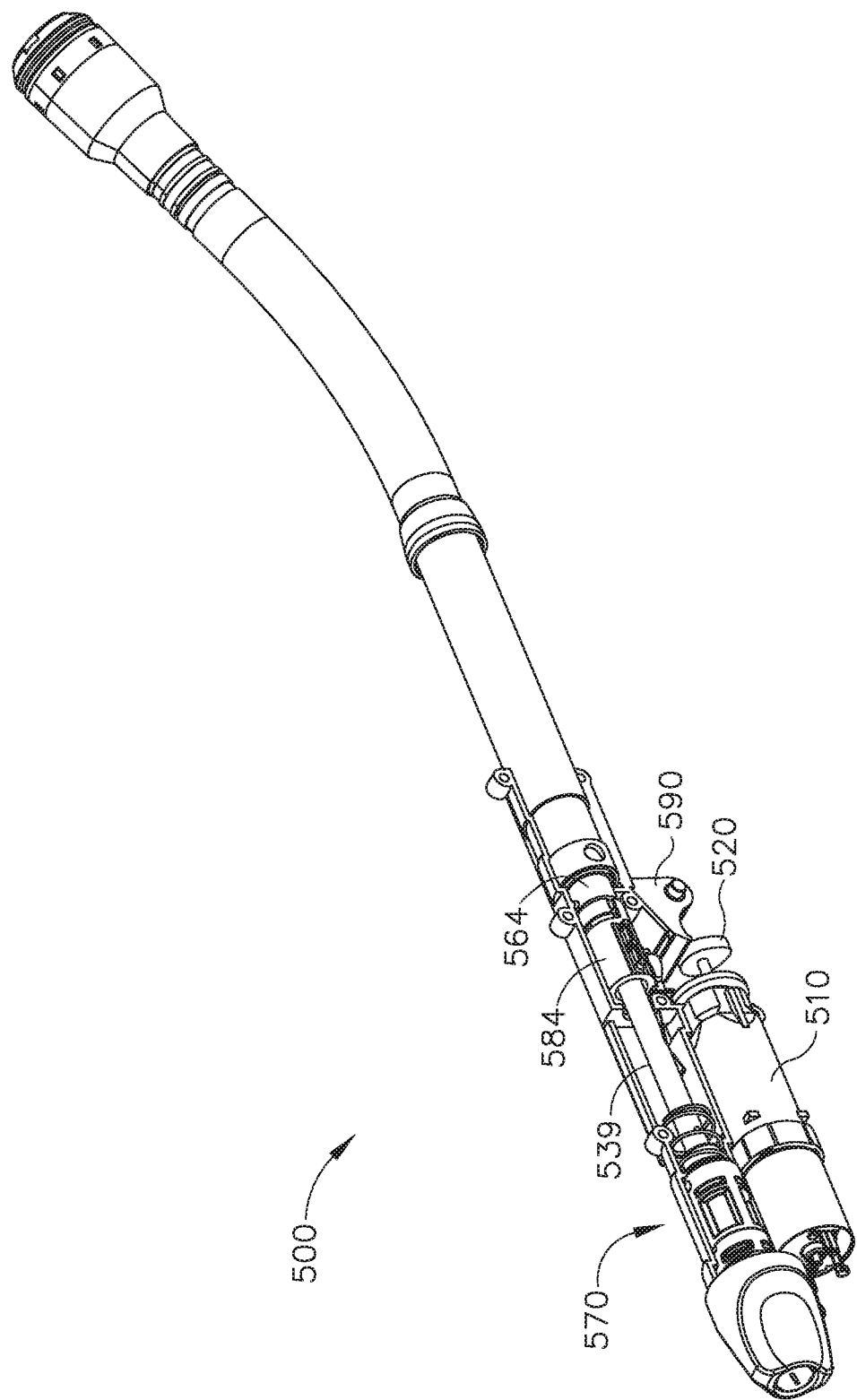
FIG. 13 depicts a perspective view of another exemplary alternative circular stapling surgical instrument having a motor and cam.
Figure 14:
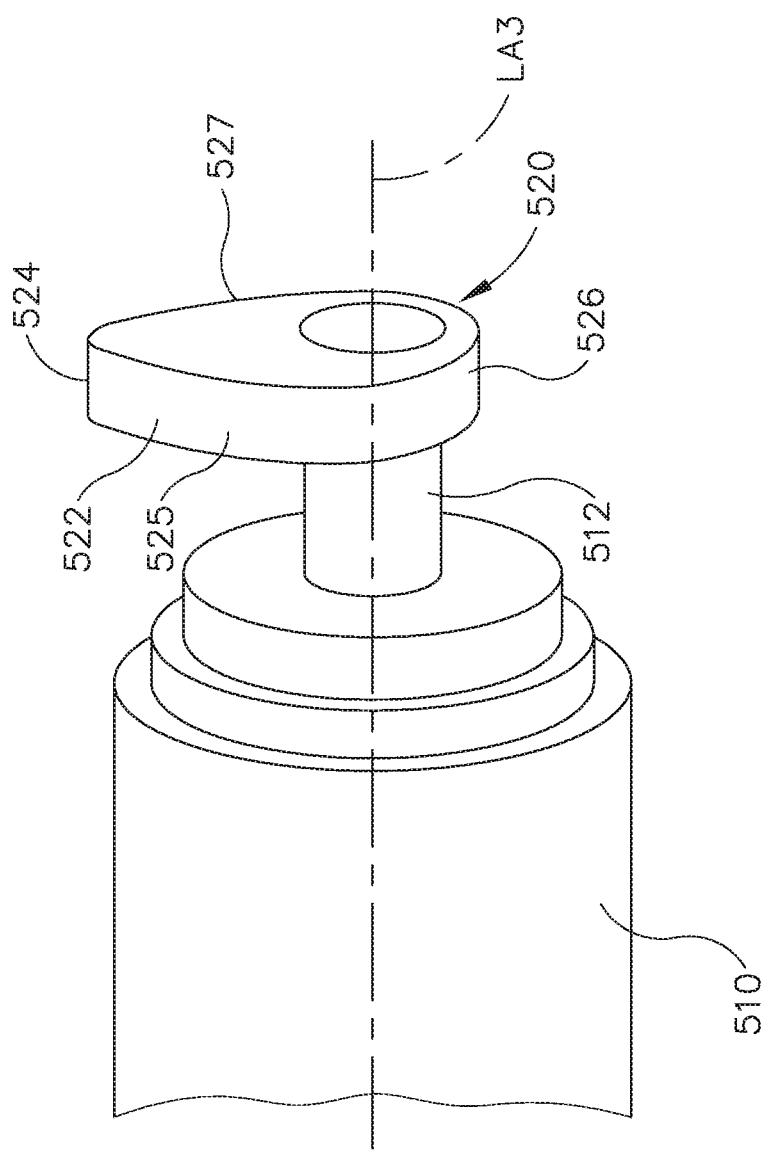
FIG. 14 depicts a perspective view of the motor and earn of FIG. 13.
Figure 15:
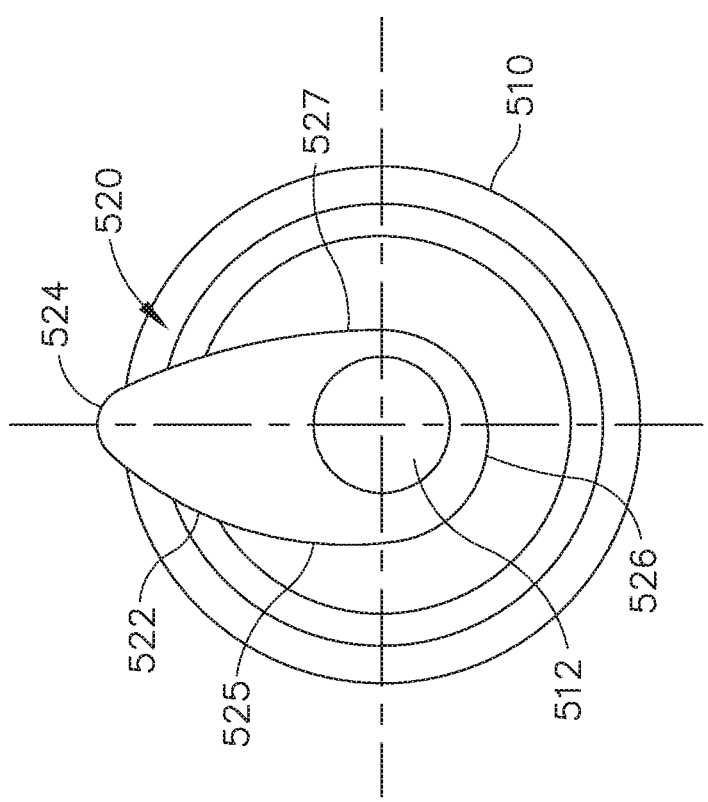
FIG. 15 depicts a front elevational view of the motor and cam of FIG. 13.

FIG. 13 shows an exemplary alternative circular surgical stapling instrument (500); while FIGS. 14-15 show a cam (520) of instrument (500) in greater detail. Instrument (500) is configured to operate substantially similar to instrument (200) discussed above except for the differences discussed below. In particular, instrument (500) may be used to staple tissue in an annular array and sever excess tissue that is interior to the annular array of staples to provide a substantially smooth transition between anastomosed tissue lumen sections. Instrument (500) comprises a motor (510) disposed within an actuator handle assembly (570) parallel to a proximal portion of a driver actuator (564). As best seen in FIG. 14, cam (520) is coupled with a distal end of motor (510) via a shaft (512). Actuation of motor (510) is configured to cause rotation of cam (520) about a longitudinal axis (LA3) defined by motor (510). In the present example, motor (510) is oriented along an axis that is parallel to the longitudinal axis defined by driver actuator (564). However, it should be understood that motor (510) may instead be oriented obliquely relative to the longitudinal axis defined by driver actuator (564). By way of example only, a merely illustrative oblique motor orientation is described in greater detail below with reference to FIGS. 22-23.

As best seen in FIGS. 14-15, an exterior surface of cam (520) comprises a first portion (524) and a second portion (526). First portion (524) and second portion (526) are disposed on radially opposite sides of cam (520). First portion (524) presents a portion of cam (520) having a radial distance from longitudinal axis (LA3) that is greater than a radial distance of second portion (526) from longitudinal axis (LA3). Cam (520) further comprises intermediate portions (525, 527) disposed between first portion (524) and second portion (526). Intermediate portions (525, 527) are contoured to provide substantially smooth transition between first portion (524) and second portion (526) along opposite sides of cam (520). Thus, it should be understood that, at a particular point along the exterior surface of cam (520), as cam (520) is rotated through one revolution, a radial distance from the exterior surface of cam (520) to longitudinal axis (LA3) will change from the lesser radial distance presented by second portion (526) to the greater radial distance presented by first portion (524) via intermediate portion (527) and back to the lesser radial distance presented by second portion (526) via intermediate portion (525).

Figure 16A:
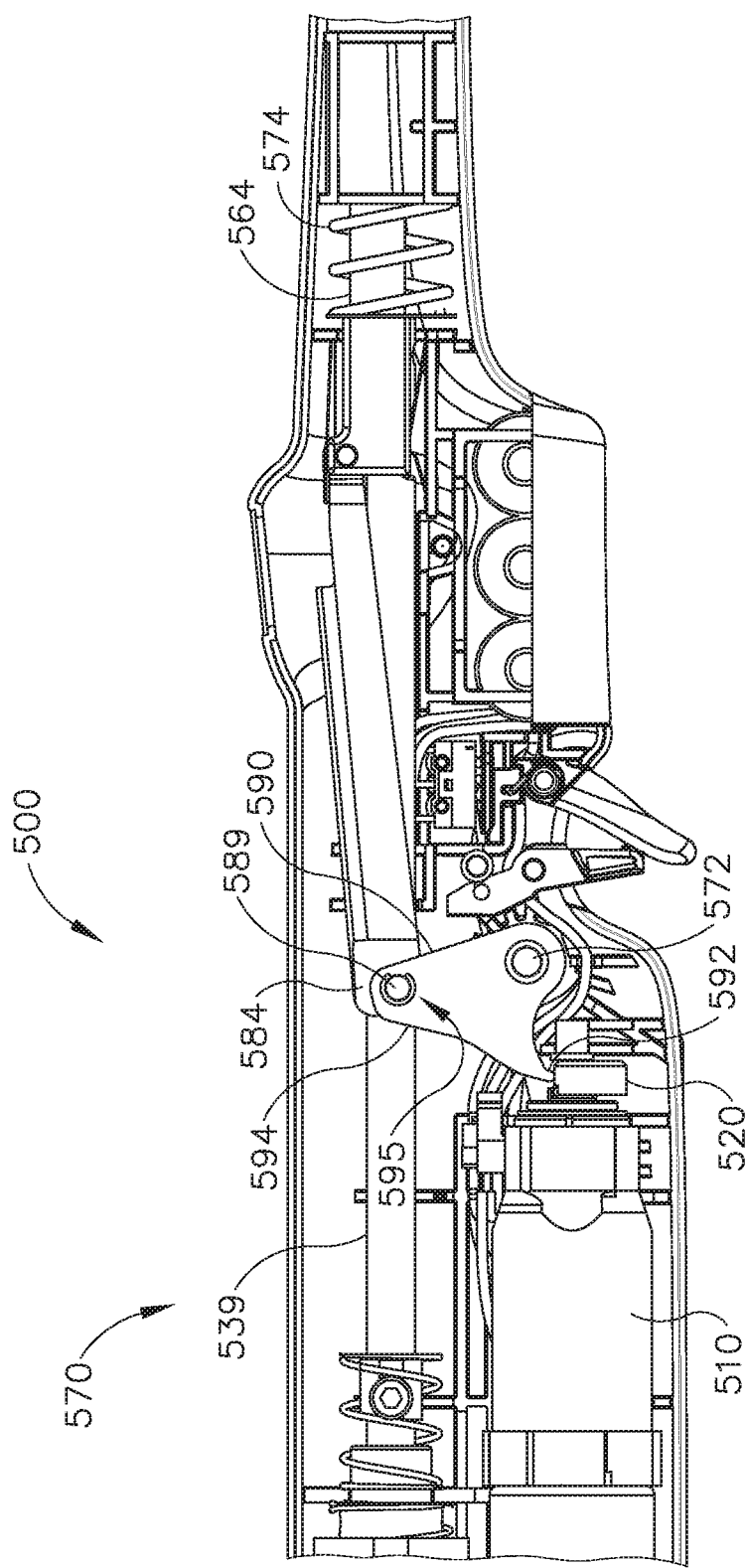
FIG. 16A depicts a side elevational view of the instrument, motor, and cam of FIG. 13 in a first rotational position.
Figure 16B:
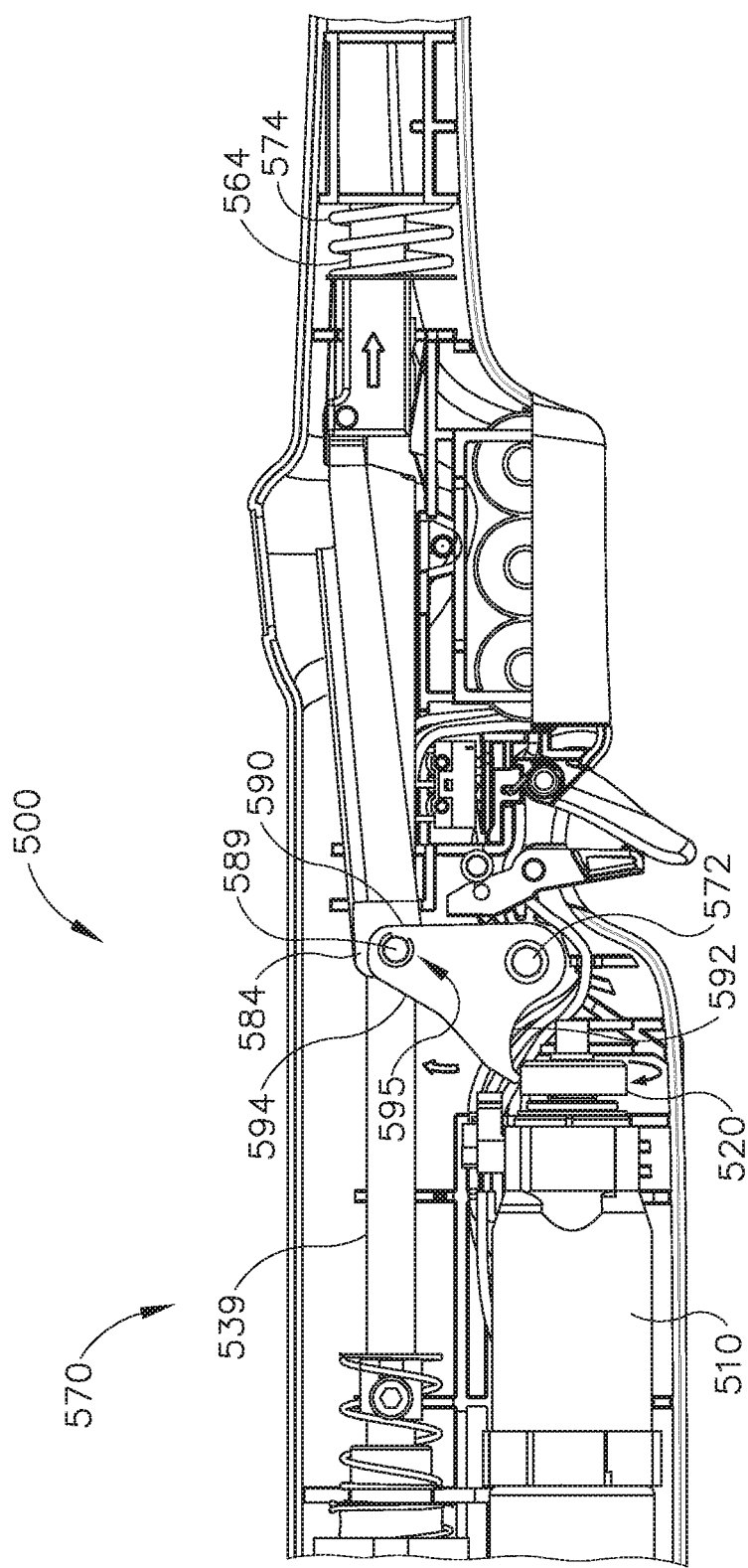
FIG. 16B depicts a side elevational view of the instrument, motor, and cam of FIG. 13 in a second rotational position.

As shown in FIGS. 16A-16B, spring (574) is disposed about driver actuator (564) within actuator handle assembly (570) and biases follower interface feature (584) longitudinally proximally. Handle assembly (570) comprises a pivot pin (572) to which a pivoting cam follower (590) is rotatably coupled such that cam follower (590) is free to rotate about pivot pin (572). A first arm (592) of cam follower (590) is in contact with the exterior surface of cam (520) due to a proximal bias imposed by a spring (574) upon follower interface feature (584). A proximal end of first arm (592) is configured to remain in contact with the exterior surface of cam (520) as cam (520) rotates. Thus, as cam (520) is rotated through one revolution, a radial distance from the proximal end of first arm (592) to longitudinal axis (LA3) will change from the lesser radial distance caused by contact with second portion (526) to the greater radial distance caused by contact with first portion (524) and back to the lesser radial distance caused by contact with second portion (526). This change of radial distance of the distal end of first arm (592) will cause cam follower (590) to rotate about pivot pin (572) from a first position (FIG. 16A) to a second position (FIG. 16B) and back to the first position (FIG. 16A).

Follower interface feature (584) comprises a pin (589) extending transversely from follower interface feature (584). Pin (589) is rotatably disposed within an opening (595) formed in a second arm (594) of cam follower (590) such that cam follower (590) is thereby coupled with follower interface feature (584) and further such that, as cam follower (590) rotates about pivot pin (572), follower interface feature (584) translates longitudinally. It should therefore be understood that, as cam (520) is rotated through one revolution, cam follower (590) is rotated from a first position to a second position and back to the first position, thus translating follower interface feature (584) from a proximal longitudinal position to a distal longitudinal position and back to the proximal longitudinal position due to the proximal bias from spring (574). This longitudinal translation of follower interface feature (584) from the proximal longitudinal position to the distal longitudinal position and back to the proximal longitudinal position will cause the staple driver to be driven from a proximal position to a distal position and back again via driver actuator (564).

As shown in FIG. 16A, with cam (520) in a first rotational position, second portion (526) of cam (520) is positioned above longitudinal axis (LA3). With cam (520) in this first rotational position, the proximal end of first arm (592) of cam follower (590) is in contact with second portion (526) of cam (520) due to the proximal bias of spring (574). At this stage, cam follower (590) is in the first position and follower interface feature (584) is in a proximal position, and thus the staple driver remains in a proximal position.

As shown in FIG. 16B, cam (520) is rotated 180° into a second rotational position. In this second rotational position, cam (520) has been rotated such that first portion (524) of cam (520) is positioned above longitudinal axis (LA3) and such that the distal end of first arm (592) of cam follower (590) is now in contact with first portion (524) of cam (520). As cam (520) is rotated from the first rotational position to the second rotational position, first arm (592) of cam follower (590) is driven from the lesser radial distance presented by second portion (526) to the greater radial distance presented by first portion (524) via intermediate portion (527), thus rotating cam follower (590) about pivot pin (572). As cam follower (590) rotates about pivot pin (572), second arm (594) is also rotated, and follower interface feature (584) is driven longitudinally distally by rotation of second arm (594) into a distal longitudinal position.

Further rotation of cam (520)—such that cam (520) has been rotated 360°—will transition cam (520) back to the first rotational position, thus allowing follower interface feature (584) to be driven proximally back into the proximal longitudinal position due to the proximal bias of spring (574). As previously discussed, this longitudinal translation of follower interface feature (584) from the proximal longitudinal position to the distal longitudinal position and back to the proximal longitudinal position will cause the staple driver to be driven from a proximal position to a distal position and back again via driver actuator (564).

As best seen in FIG. 15, intermediate portion (525) and intermediate portion (527) have different contours. These different contours represent different rates of change of the radial distance from the outwardly facing caroming surface of channel (522) to longitudinal axis (LA3) presented by first portion (524) to second portion (526) and vice versa. In particular, intermediate portion (525) represents a more gradual rate of change from the radial distance presented by second portion (526) to the radial distance presented by first portion (524) whereas intermediate portion (527) represents a more rapid rate of change from the radial distance presented by first portion (524) to the radial distance presented by second portion (526) or vice versa depending on the direction in which cam (520) is rotated. It should be understood that these differing rates of change will be communicated to follower interface feature (584), driver actuator (564), and the staple driver via cam follower (590) thus imparting varying mechanical advantage to and causing differing rates of longitudinal translation of follower interface feature (584), driver actuator (564), and the staple driver. For instance, intermediate portion (525) may provide a relatively slow rate of distal advancement of driver actuator (564) while intermediate portion (527) provides a relatively rapid rate of proximal retraction of driver actuator (564). Of course, these rates may be further varied in any suitable way.

1. First Exemplary Reduced Friction Pivoting Member

It may be desirable to minimize the force require to rotate cam (520). Such a reduction in force may be accomplished by reducing the force required to rotate cam follower (590) about pivoting pin (572). One merely exemplary variation of a reduced-friction pivoting cam follower (690) is shown in FIG. 18. Cam follower (690) is configured to operate substantially similar to cam follower (590) discussed above. In particular, cam follower (690) is configured to rotate about a pivot pin and thus longitudinally translate follower interface feature (584) as a result of cam (520) being rotated by motor (510). Cam follower (690) comprises a first arm (692) configured to operate substantially similar to first arm (592) of cam follower (590). In particular, a distal end of first arm (692) is configured to contact cam (520) as cam (520) rotates to longitudinally translate driver actuator (564). A distal end of first arm (692) of cam follower (690) presents a curved edge (693). Curved edge (693) is configured to contact the exterior surface of cam (520) as cam (520) rotates. As shown in FIG. 17, the distal end of first arm (592) of cam follower (590) from the previous example presents a flat edge (593). It should be understood that curved edge (693) of cam follower (690) may reduce the friction between cam follower (690) and cam (520) as compared with friction between flat edge (593) of cam follower (590) and cam (520).

In addition or in the alternative, the curved configuration of curved edge (693) may provide a more efficient transfer of force from cam (520) to cam follower (690). While cam (520) rotates, laterally oriented forces imparted from rotating cam (520) to flat edge (593) might be lost to friction and converted to heat, without actually causing cam follower (590) to pivot. By contrast, curved edge (693) may be able to convert some of those same laterally oriented forces into pivoting motion of cam follower (690), by effectively receiving vertical components of the normal force and converting the same into pivotal movement of cam follower (690). Therefore, curved edge (693) may provide a more productive and/or efficient transfer of force from cam (520) to cam follower (690) along a greater range of rotation of cam (520).

2. Second Exemplary Reduced Friction Pivoting Member

Figure 19A:
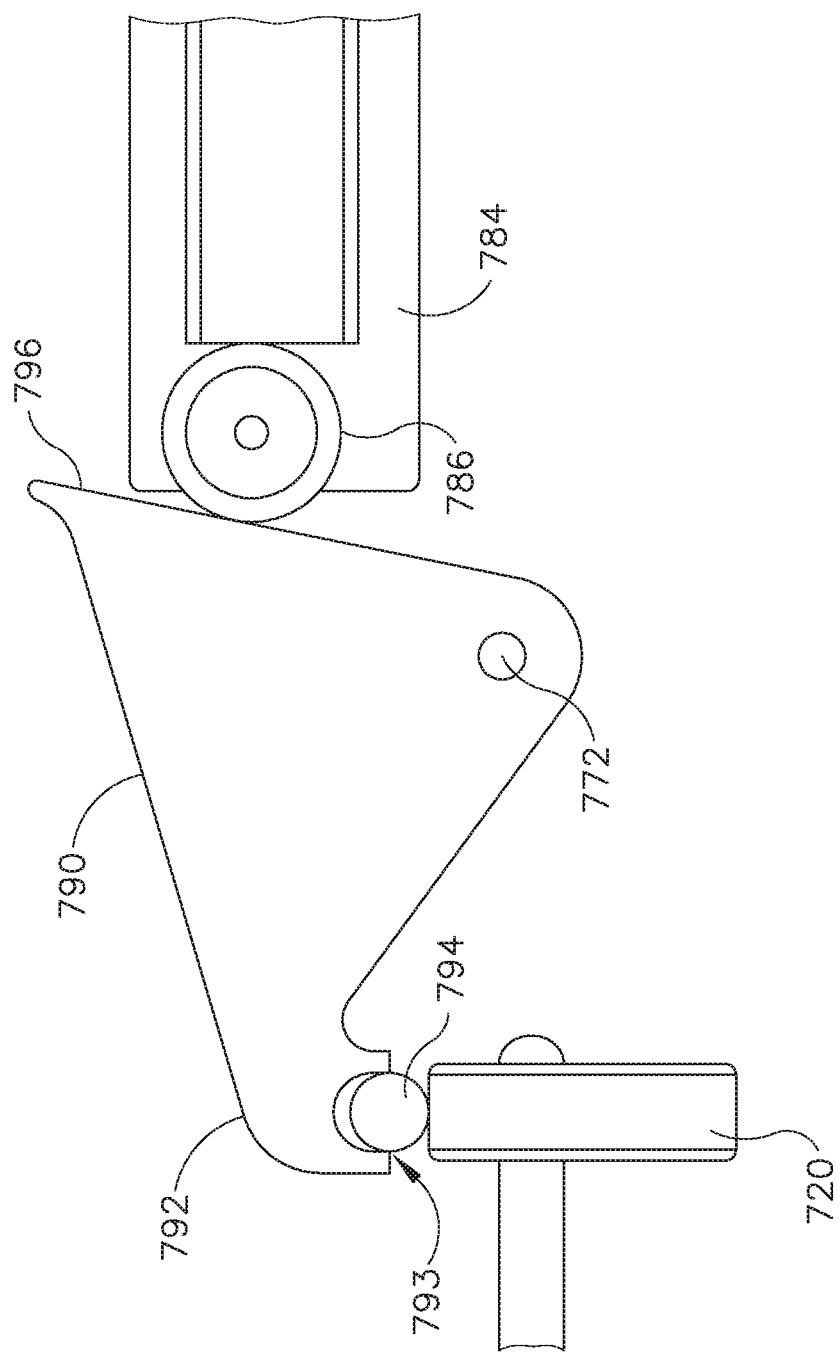
FIG. 19A depicts a side elevational view of an exemplary firing arm assembly that may be incorporated into the instrument of FIG. 13, in a first position.
Figure 19B:
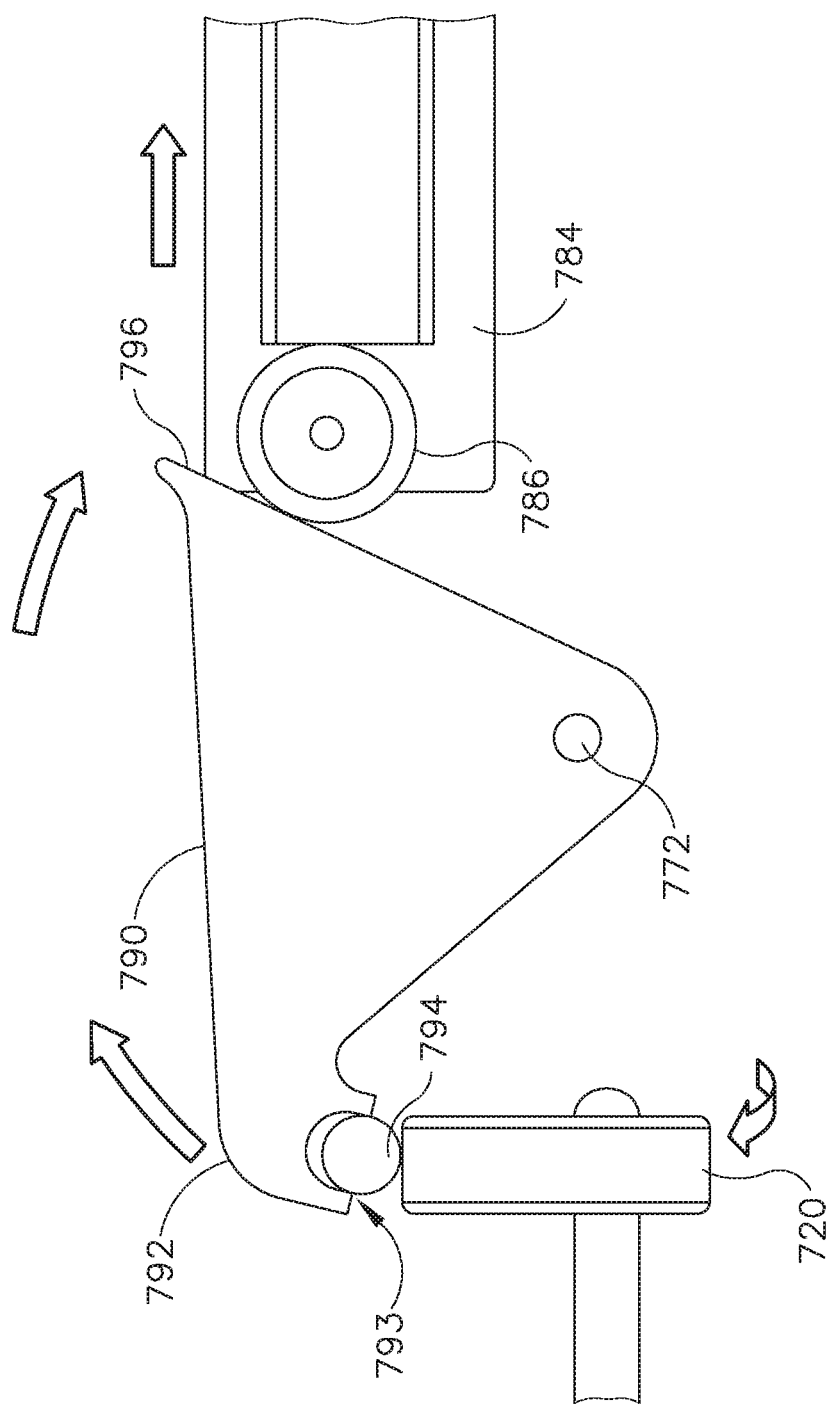
FIG. 19B depicts a side elevational view of the exemplary firing arm assembly of FIG. 19A in a second position.

FIGS. 19A-19B show another merely exemplary variation of a reduced-friction pivoting cam follower (790). Cam follower (790) is configured to operate substantially similar to cam follower (590) discussed above except for the differences discussed below. In particular, as shown in FIG. 19B, cam follower (790) is configured to rotate about a pivot pin (772) and thus longitudinally translate a follower interface feature (784) as a result of a cam (720) being rotated by a motor (not shown). Follower interface feature (784) is configured to operate substantially similar to follower interface feature (584) discussed above except for the differences discussed below. In particular, longitudinal translation of follower interface feature (784) causes longitudinal translation of a staple driver and knife (not shown).

Cam follower (790) comprises a first portion (792) configured to operate substantially similar to first arm (592) of cam follower (590) except for the differences discussed below. In particular, a proximal end of first portion (792) is associated with an exterior surface of cam (720) such that rotation of cam (720) causes rotation of cam follower (790), which in turn causes longitudinal translation of follower interface feature (784). A proximal end of first portion (792) of cam follower (790) presents a socket (793). A ball bearing (794) is rotatably positioned within socket (793). Ball bearing (794) is configured to contact the exterior surface of cam (720) as cam (720) rotates. It should be understood that ball bearing (794) may reduce the friction between cam follower (790) and cam (720) as compared to friction between cam follower (590) and cam (520). It should further be understood that the curved surface of ball bearing (794) may providing a more productive and/or efficient transfer of force from cam (720) to cam follower (790) along a greater range of rotation of cam (720).

As also shown in FIGS. 19A-19B, a proximal end of follower interface feature (784) of the present example comprises a wheel (786). Wheel (786) is freely rotatable relative to follower interface feature (784). Cam follower (790) comprises a second portion (796) configured to operate substantially similar to second arm (592) of cam follower (590) except for the differences discussed below. In particular, rotation of cam follower (790) is configured to longitudinally translate follower interface feature (784) via second portion (792). Second portion (796) contacts wheel (786) such that as cam follower (790) rotates, second portion (796) will ride along and rotate wheel (786) while simultaneously driving follower interface feature (784) distally. It should be understood that wheel (786) may reduce the friction between cam follower (790) and follower interface feature (784) as compared with friction between cam follower (590) and follower interface feature (584).

Although the present example comprises both ball bearing (794) and wheel (786), cam follower (790) and follower interface feature (784) need not include both ball bearing (794) and wheel (786). For instance, some versions may include ball bearing (794) but lack wheel (786). As another merely illustrative example, some versions may include wheel (786) but lack ball bearing (794). Other suitable configurations and arrangements will be apparent to those of ordinary skill in the art in view of the teachings herein.

3. Third Exemplary Reduced Friction Pivoting Member

Figure 20A:
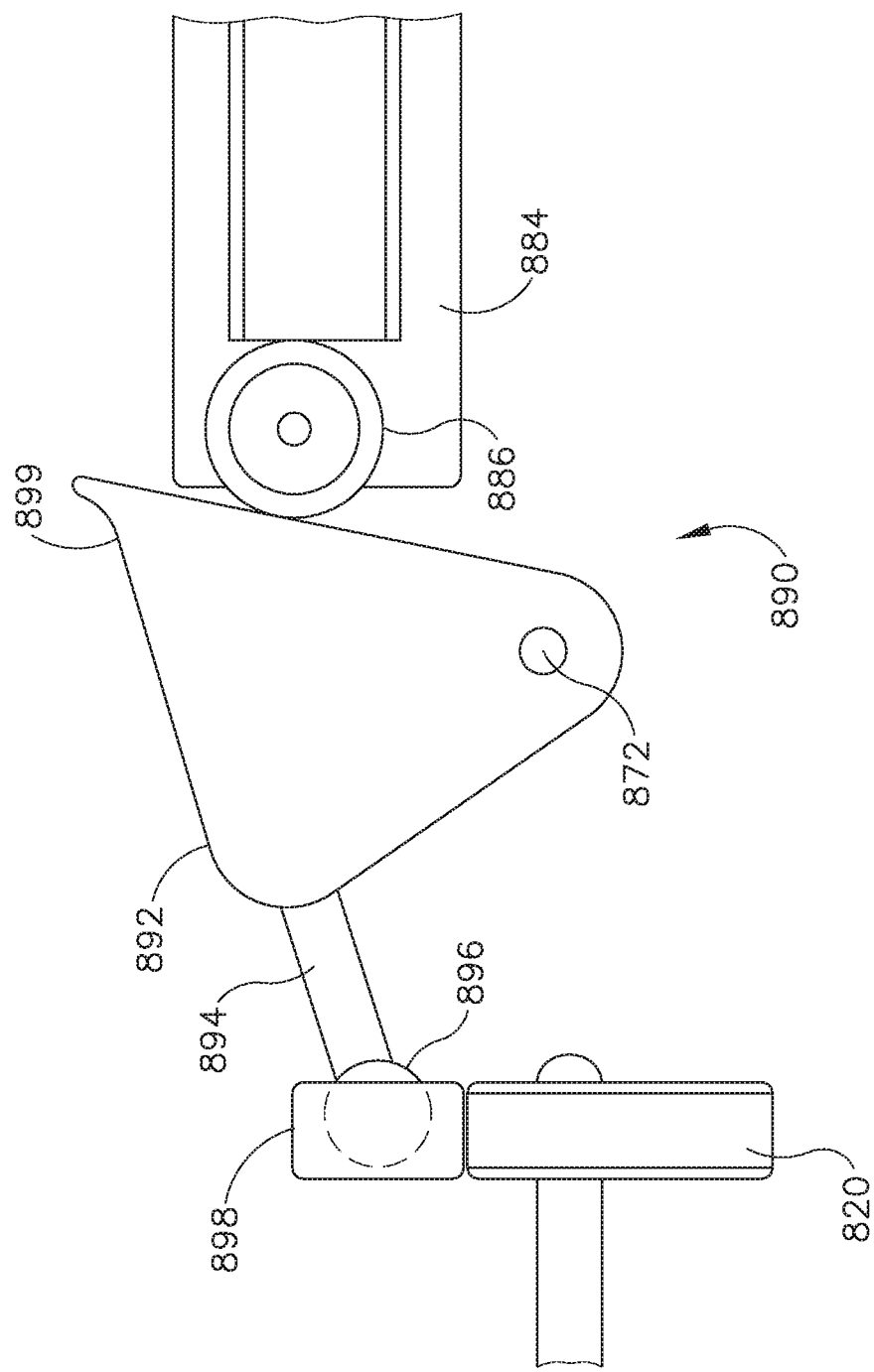
FIG. 20A depicts a side elevational view of another exemplary firing arm assembly that may be incorporated into the instrument of FIG. 13, in a first position.
Figure 20B:
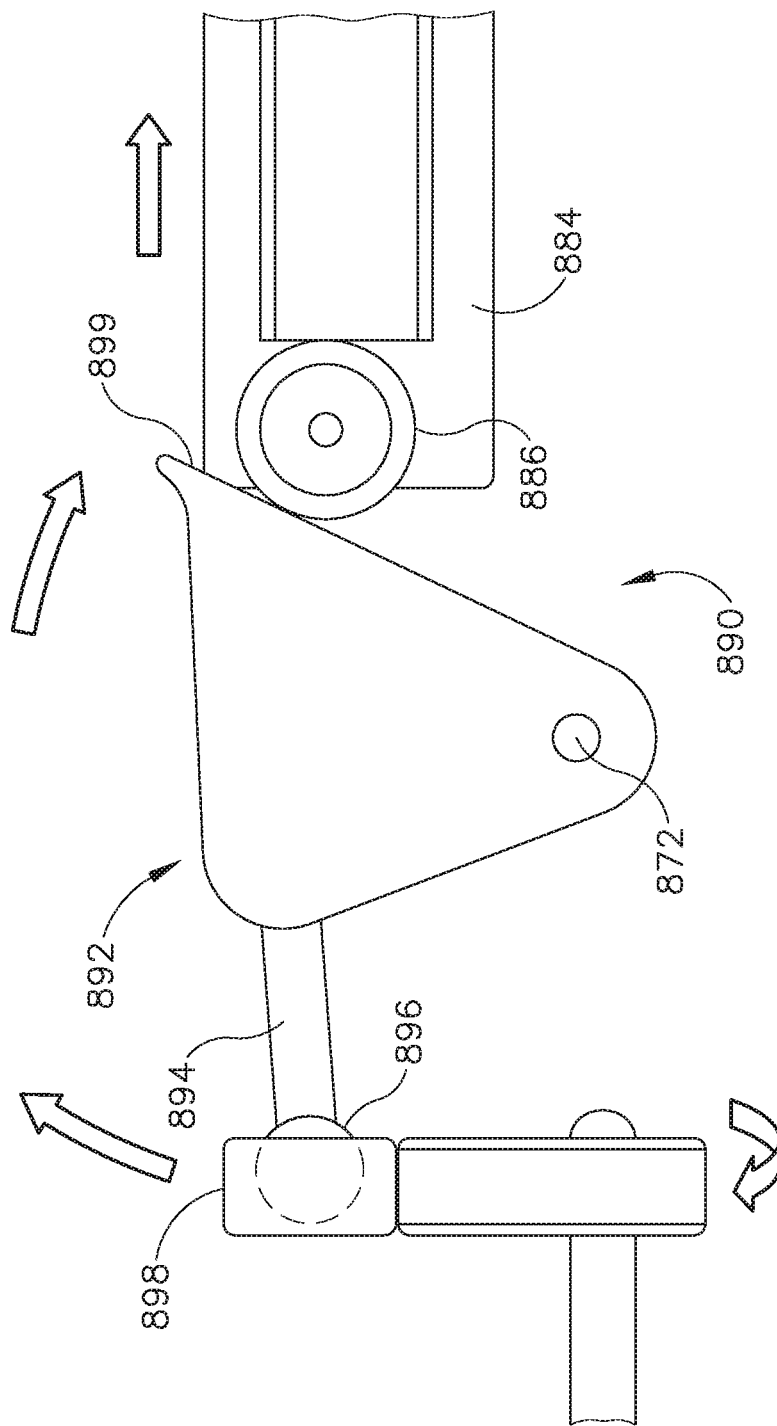
FIG. 20B depicts a side elevational view of the exemplary firing arm assembly of FIG. 20A in a second position.

Yet another merely exemplary variation of a reduced-friction pivoting cam follower (890) is shown in FIGS. 20A-20B. Cam follower (890) is configured to operate substantially similar to cam follower (590) discussed above except for the differences discussed below. In particular, as shown in FIG. 20B, cam follower (890) is configured to rotate about a pivot pin (872) and thus longitudinally translate a follower interface feature (884) as a result of a cam (820) being rotated by a motor (not shown). Follower interface feature (884) is configured to operate substantially similar to follower interface feature (584) discussed above except for the differences discussed below. In particular, longitudinal translation of follower interface feature (884) causes longitudinal translation of a staple driver (not shown).

Cam follower (890) comprises a first portion (892) configured to operate substantially similar to first arm (592) of cam follower (590) except for the differences discussed below. In particular, a proximal end of first portion (892) is associated with an exterior surface of cam (820) such that rotation of cam (820) causes rotation of cam follower (890), which in turn causes longitudinal translation of follower interface feature (884). A proximal end of first portion (892) of cam follower (890) of the present example is rigidly coupled to a shaft (894). A proximal end of shaft (894) comprises a ball (896). Ball (896) is rotatably secured within a socket formed in a cylinder (898) such that ball (896) is free to rotate within cylinder (898). Cylinder (898) is positioned to contact the exterior surface of cam (820) as cam (820) rotates such that rotation of cam (820) causes rotation of cylinder (898) about ball (896). It should be understood that ball (896) and cylinder (898) may reduce the friction between cam follower (890) and cam (820) as compared to friction between cam follower (590) and cam (520).

As further shown in FIGS. 20A-20B, a proximal end of follower interface feature (884) of the present example comprises a wheel (886). Cam follower (890) comprises a second portion (899) configured to operate substantially similar to second arm (592) of cam follower (590) except for the differences discussed below. In particular, rotation of cam follower (890) is configured to longitudinally translate follower interface feature (884) via second portion (899). Second portion (899) contacts wheel (886) such that as cam follower (890) rotates, second portion (899) will ride along and rotate wheel (886) while simultaneously driving follower interface feature (884) distally. It should be understood that wheel (886) may reduce the friction between cam follower (890) and follower interface feature (884) as compared to friction between cam follower (590) and follower interface feature (584).

Although the present example comprises ball (896), cylinder (898), and wheel (886), cam follower (890) and follower interface feature (884) need not include each of ball (896), cylinder (898), and wheel (886). For instance, some versions may include ball (896) and cylinder (898) but lack wheel (886). As another merely illustrative example, some versions may include wheel (886) but lack ball (896) and cylinder (898). Other suitable configurations and arrangements will be apparent to those of ordinary skill in the art in view of the teachings herein.

IV. EXEMPLARY MOTORIZED CIRCULAR SURGICAL STAPLING INSTRUMENT WITH DUAL MOTORS

As a variation of instrument (200) discussed above, instrument (200) may be provided with a plurality of motors. In particular, handle assembly (270) may be reconfigured to accommodate a plurality of motors to actuate the staple driver. By way of example only, a plurality of motors may be desirable in order to drive staples through and/or cut thick or coarse tissue. Various examples of how instrument (200) may be reconfigured to incorporate a plurality of motors will be described in greater detail below; while other examples will be apparent to those of ordinary skill in the art according to the teachings herein. It should be understood that the examples described below may function substantially similar to instrument (200) described above. In particular, the variations of circular surgical stapling instrument (200) described below may be used to staple tissue in an annular array and sever excess tissue that is interior to the annular array of staples to provide a substantially smooth transition between lumen sections.

Figure 21:
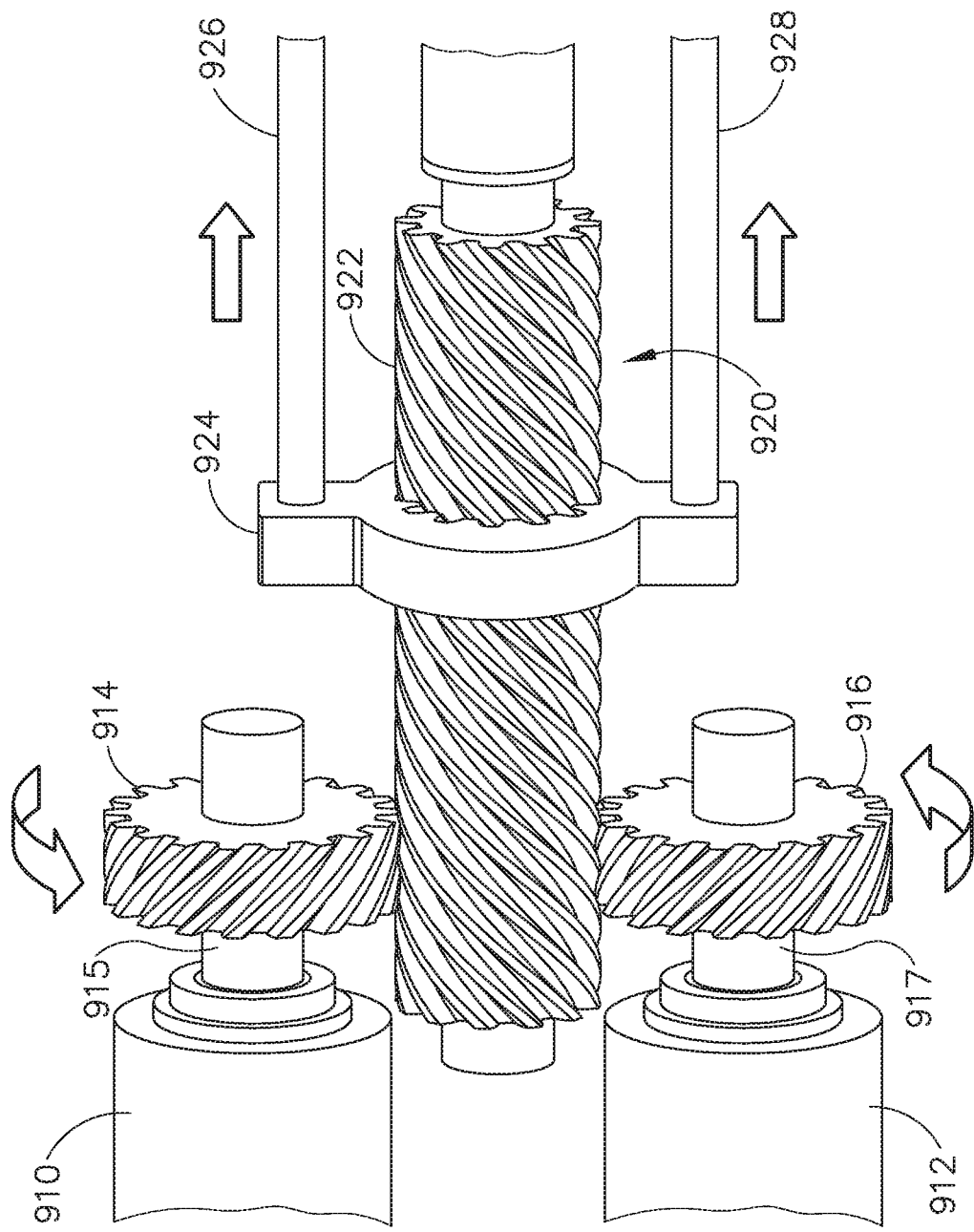
FIG. 21 depicts a perspective view of an exemplary multi-motor firing assembly.

FIG. 21 shows exemplary alternative components that may be incorporated into instrument (200) to actuate the staple driver and knife. In particular, FIG. 21 shows a first motor (910), a second motor (912), and other components coupled with motors (910, 912). Motors (910, 912) of the present example may be powered by an internal power source (e.g., battery, etc.) and/or an external power source (e.g., wall outlet, etc.). As will be discussed in more detail below, motors (910, 912) are configured to actuate a staple driver. The staple driver includes a plurality of staple driving members, a plurality of staples, and a knife configured to sever tissue when the staple driver is actuated longitudinally. The staple driver of the present example functions substantially similar to the staple driver of instrument (200) described above. In particular, the staple driver of the present example may be used to drive an annular array of staples into tissue and to drive a knife (not shown) to sever excess tissue that is interior to the annular array of staples to provide a substantially smooth transition between lumen sections in response to the staple driver being actuated.

A proximal end of a driver actuator (not shown) is coupled to shafts (926, 928), which are described in greater detail below, and which may be positioned within an actuator handle assembly (not shown). A distal end of the driver actuator is coupled to the staple driver such that longitudinal translation of shafts (926, 928) actuates the staple driver via the driver actuator. As will be discussed in more detail below, motors (910, 912) are operable to cause longitudinal translation of shafts (926, 928) via a drive assembly. Thus, when motors (910, 912) are actuated and translate shafts (926, 928), the knife and the staple driving members substantially simultaneously sever tissue and drive staples distally into tissue.

Motors (910, 912) are disposed along different axes within the actuator handle assembly. Motors (910, 912) rotate their respective drive shafts (915, 917) in opposite directions. A first helical gear (914) is secured to a distal end of motor (914) via shaft (915). A second helical gear (916) is secured to a distal end of motor (912) via shaft (917). A driven shaft (920) presents helical threading (922). Shaft (920) is disposed within and rotatably secured to the actuator handle assembly such that helical threading (922) engages both first helical gear (914) and second helical gear (916). First helical gear (914) and second helical gear (916) engage helical threading (922) on radially opposite sides of shaft (920). A drive nut (924) is disposed about shaft (920) and engages helical threading (922) such that rotation of shaft (920) causes longitudinal translation of drive nut (924). A pair of shafts (926, 928) extends distally from drive nut (924). The distal ends of shafts (926, 928) are secured to the driver actuator such that longitudinal translation of drive nut (924) causes concurrent longitudinal translation of the driver actuator. It should therefore be understood that rotation of motors (910, 912) causes longitudinal translation of the staple driver via the driver actuator.

Motors (910, 912) may be actuated such that motors (910, 912) rotate shaft (920) in a first direction to drive shafts (926, 928) distally from a proximal longitudinal position to a distal longitudinal position. Motors (910, 912) may then be reversed such that motors (910, 912) rotate shaft (920) in a second direction to drive shafts (926, 928) proximally back to the proximal longitudinal position. This longitudinal translation of shafts (926, 928) from the proximal longitudinal position to the distal longitudinal position and back to the proximal longitudinal position will cause the staple driver to be driven from a proximal position to a distal position and back again via the driver actuator. Other suitable ways in which motors (910, 912) may be operated will be apparent to those of ordinary skill in the art in view of the teachings herein.

V. EXEMPLARY OBLIQUE MOTOR ORIENTATION

Figure 22:
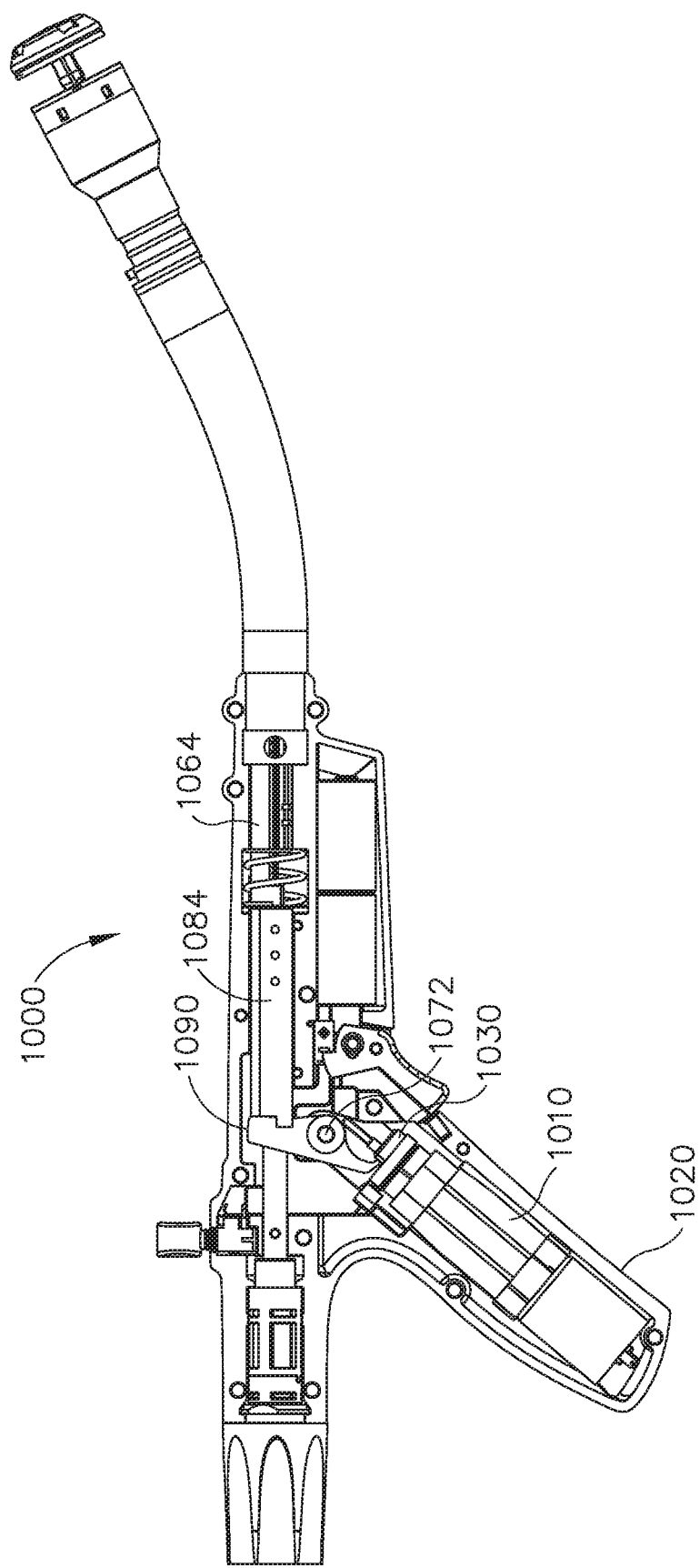
FIG. 22 depicts a side elevational view of an exemplary alternative circular stapling surgical instrument having an obliquely oriented motor.

Although the examples discussed above comprise a motor(s) disposed within an actuator handle assembly at an orientation that is parallel to a proximal portion of a driver actuator, it should be understood that the motor(s) may be oriented in other suitable orientation. For instance, as shown in FIG. 22, a motor (1010) may be disposed within an oblique pistol grip (1020) of a circular surgical stapling instrument (1000) such that motor (1010) is oriented obliquely to a longitudinal axis defined by a driver actuator (1064). A cam (1030) is secured to motor (1010) such that actuation of motor (1010) rotates cam (1030). A pivoting cam follower (890) rotates about a pivot pin (1072). Cam follower (890) is configured to operate substantially similar to cam follower (590) discussed above. In particular, cam follower (890) is associated with cam (1030) and a follower interface feature (1084) such that rotation of cam follower (890) causes longitudinal translation of follower interface feature (1084). It should be understood that, cam (1030) could be configured in accordance with any of the cams (320, 420, 520) or cam assembly (220) discussed above. It should also be understood that the present example is merely illustrative. Other appropriate motor orientations will be apparent to those of ordinary skill in the art in view of the teachings herein.

Figure 23:
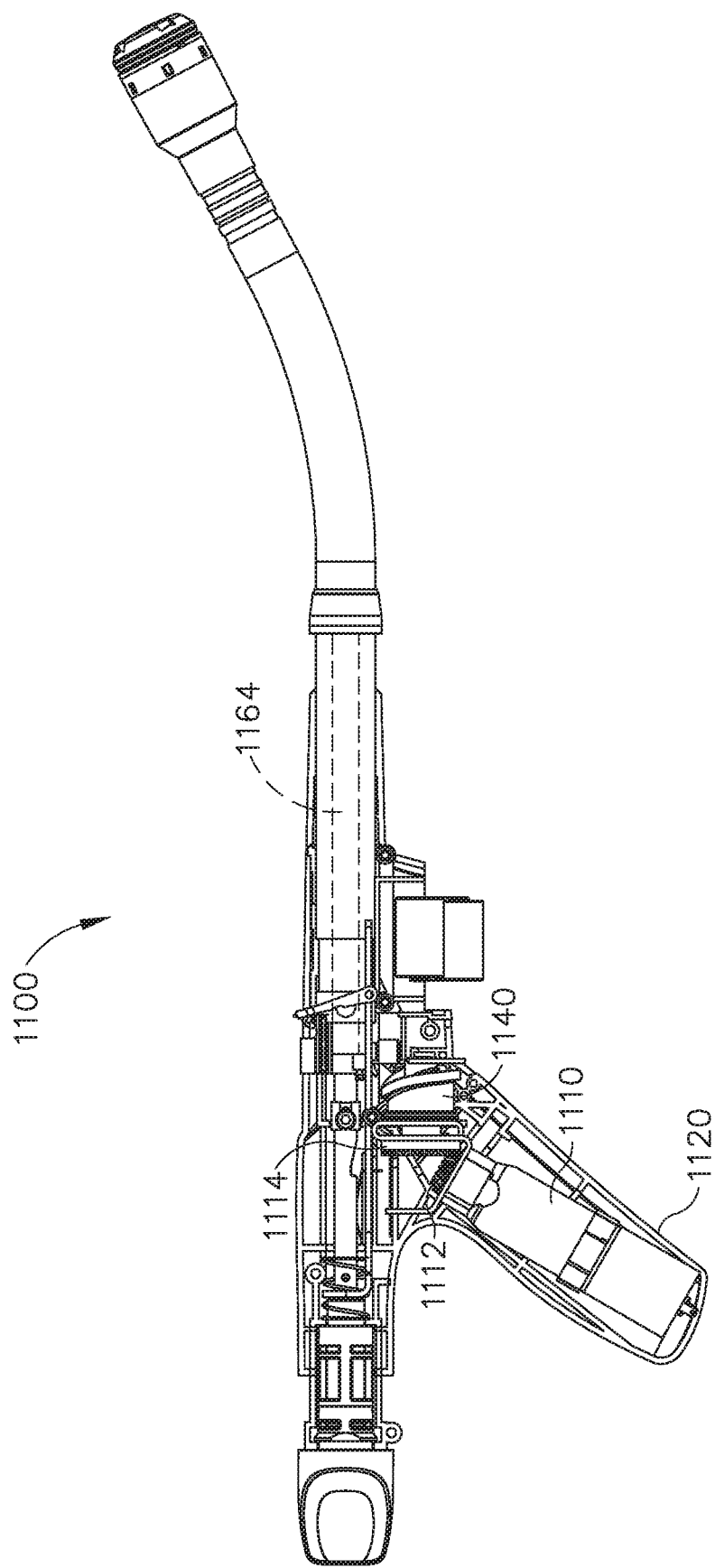
FIG. 23 depicts a perspective view of another exemplary alternative circular stapling surgical instrument having an obliquely oriented motor.

As shown in FIG. 23, a motor (1110) may be disposed within an oblique pistol grip (1120) of a circular surgical stapling instrument (1100) such that motor (1110) is oriented obliquely to a longitudinal axis defined by a driver actuator (1164). A first beveled gear (1112) is secured to motor (1110) such that rotation of motor (1110) causes rotation of beveled gear (1112). A second beveled gear (1114) is secured to a proximal end of cam (1140). First beveled gear (1112) and second beveled gear (1114) engage such that rotation of first beveled gear (1112) causes rotation of second beveled gear (1114). Rotation of motor (1110) will thus cause rotation of cam (1140). It should be understood that cam (1140) could be configured in accordance with any of the cams (320, 420, 520) or cam assembly (220) discussed above. It should also be understood that the present example is merely illustrative. Other suitable ways of achieving oblique motor orientations will be apparent to those of ordinary skill in the art in view of the teachings herein. By way of example only, a handle assembly may provide a perpendicularly oriented or obliquely oriented pistol grip and/or motor in accordance with the teachings of U.S. Pat. Pub. No. 2015/0083772, entitled SURGICAL STAPLER WITH ROTARY CAM DRIVE AND RETURN, published Mar. 26, 2015, now abandoned, the disclosure of which is incorporated by reference herein.

VI. MISCELLANEOUS

In any of the examples described above, a microcontroller, ASIC, and/or other type of control module may be placed in communication with a power source and motor (210, 310, 410, 510) and may be configured to automatically stop motor (210, 310, 410, 510) thereby providing a way to dynamically brake motor (210, 310, 410, 510) such that motor (210, 310, 410, 510) may be actuated for exactly one rotation of a corresponding drive shaft. By way of example only, such a control module may be in communication with an encoder that is in communication with the drive shaft or some other component that moves in response to activation of motor (210, 310, 410, 510). As another merely illustrative example, such a control module may be in communication with one or more reed switches that are in communication with the drive shaft or some other component that moves in response to activation of motor (210, 310, 410, 510). Other suitable types of sensors and control modules that may be used to provide precise stopping of motor (210, 310, 410, 510) (e.g., based on tracked rotation of a component, based on translation of a component, and/or based on some other parameter, etc.) will be apparent to those of ordinary skill in the art in view of the teachings herein. Of course, a control module may be configured to control motor (210, 310, 410, 510) to activate for any suitable number of rotations, etc. In some instances, controlling the starting and stopping of motor (210, 310, 410, 510) may be performed in accordance with the teachings of U.S. Pat. Pub. No. 2015/0083774, entitled CONTROL FEATURES FOR MOTORIZED SURGICAL STAPLING INSTRUMENT, published Mar. 26, 2015, issued as U.S. Pat. No. 9,907,552 on Mar. 6, 2018, the disclosure of which is incorporated by reference herein.

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

At least some of the teachings herein may be readily combined with one or more teachings of U.S. Pat. No. 7,794,475, entitled "Surgical Staples Having Compressible or Crushable Members for Securing Tissue Therein and Stapling Instruments for Deploying the Same," issued Sep. 14, 2010, the disclosure of which is incorporated by reference herein; U.S. patent application Ser. No. 13/693,430, entitled "Trans-Oral Circular Anvil Introduction System with Dilation Feature," filed Dec. 4, 2012, now U.S. Pat. No. 9,572,573, issued on Feb. 21, 2017, the disclosure of which is incorporated by reference herein; U.S. patent application Ser. No. 13/688,951, entitled "Surgical Staple with Integral Pledget for Tip Deflection," filed Nov. 29, 2012, now U.S. Pat. No. 9,289,207, issued on Mar. 22, 2016, the disclosure of which is incorporated by reference herein; U.S. patent application Ser. No. 13/706,827, entitled "Surgical Stapler with Varying Staple Widths along Different Circumferences," filed Dec. 6, 2012, published as U.S. Pub. No. 2014/0158747 on Jun. 12, 2014, now abandoned, the disclosure of which is incorporated by reference herein; U.S. patent application Ser. No. 13/688,992, entitled "Pivoting Anvil for Surgical Circular Stapler," filed Nov. 29, 2012, now U.S. Pat. No. 9,498,222, issued on Nov. 22, 2016, the disclosure of which is incorporated by reference herein; U.S. patent application Ser. No. 13/693,455, entitled "Circular Anvil Introduction System with Alignment Feature," filed Dec. 4, 2012, published as U.S. Pub. No. 2014/0151430 on Jun. 5, 2014, issued as U.S. Pat. No. 9,724,100 on Aug. 8, 2017, the disclosure of which is incorporated by reference herein; U.S. patent application Ser. No. 13/716,313, entitled "Circular Stapler with Selectable Motorized and Manual Control, Including a Control Ring," filed Dec. 17, 2012, now U.S. Pat. No. 9,532,783, issued on Jan. 3, 2017, the disclosure of which is incorporated by reference herein; U.S. patent application Ser. No. 13/716,318, entitled "Motor Driven Rotary Input Circular Stapler with Modular End Effector," filed Dec. 17, 2012, now U.S. Pat. No. 9,597,081, issued on Mar. 21, 2017, the disclosure of which is incorporated by reference herein; and/or U.S. patent application Ser. No. 13/176,323, entitled "Motor Driven Rotary Input Circular Stapler with Lockable Flexible Shaft," filed Dec. 17, 2012, published as U.S. Pub. No. 2011/0261666 on Oct. 27, 2011, now abandoned, the disclosure of which is incorporated by reference herein. Various suitable ways in which such teachings may be combined will be apparent to those of ordinary skill in the art.

While the examples herein have been provided in the context of a circular stapling instrument, it should be understood that the various teachings herein may be readily applied to various other kinds of surgical instruments. By way of example only, the various teachings herein may be readily applied to linear stapling devices (e.g., endocutters). For instance, various teachings herein may be readily combined with various teachings of U.S. Pub. No. 2012/0239012, entitled "Motor-Driven Surgical Cutting Instrument with Electric Actuator Directional Control Assembly," published Sep. 20, 2012, now U.S. Pat. No. 8,453,914, issued on Jun. 4, 2013, the disclosure of which is incorporated by reference herein, and/or U.S. Pub. No. 2010/0264193, entitled "Surgical Stapling Instrument with An Articulatable End Effector," published Oct. 21, 2010, now U.S. Pat. No. 8,408,439, issued on Apr. 2, 2013, the disclosure of which is incorporated by reference herein, as will be apparent to those of ordinary skill in the art. As another merely illustrative example, the various teachings herein may be readily applied to a motorized electrosurgical device. For instance, various teachings herein may be readily combined with various teachings of U.S. Pub. No. 2012/0116379, entitled "Motor Driven Electrosurgical Device with Mechanical and Electrical Feedback," published May 10, 2012, now U.S. Pat. No. 9,161,803, issued on Oct. 20, 2015, the disclosure of which is incorporated by reference herein, as will be apparent to those of ordinary skill in the art. Other suitable kinds of instruments in which the teachings herein may be applied, and various ways in which the teachings herein may be applied to such instruments, will be apparent to those of ordinary skill in the art.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A surgical instrument comprising:
   (a) a body;
   (b) a shaft extending distally from the body, wherein the shaft comprises a proximal end and a distal end;
   (c) a stapling assembly, wherein the stapling assembly is disposed at the distal end of the shaft, wherein the stapling assembly is operable to drive a plurality of staples into tissue;
   (d) a motor;
   (e) a cam assembly coupled with the motor, wherein the cam assembly includes a first cam portion and a second cam portion, wherein the motor is operable to rotate the first and second cam portions, wherein the first and second cam portions are configured to remain longitudinally stationary relative to the motor during rotation by the motor; and
   (f) a firing assembly having a distal firing portion operatively coupled with the stapling assembly, wherein the distal firing portion is configured to move distally from a proximal position to a distal position and thereby drive movement of the stapling assembly,
   wherein the first and second cam portions are configured to sequentially engage the firing assembly during rotation of the cam assembly relative to the firing assembly such that:
      (i) the first cam portion drives the distal firing portion distally toward the distal position through a first segment of longitudinal travel, and
      (ii) the second cam portion drives the distal firing portion further distally toward the distal position through a second segment of longitudinal travel that extends distally from the first segment of longitudinal travel, wherein the first and second segments of longitudinal travel differ in length.

2. The surgical instrument of claim 1, wherein the firing assembly includes a follower member operatively coupled to the body and to the distal firing portion, wherein the follower member includes a first follower portion and a second follower portion, wherein the first cam portion is configured to contact the first follower portion to drive the distal firing portion through the first segment of longitudinal travel, wherein the second cam portion is configured to contact the second follower portion to drive the distal firing portion through the second segment of longitudinal travel.

3. The surgical instrument of claim 2, wherein the follower member is pivotably coupled to the body about a pivot axis, wherein the follower member is configured to pivot about the pivot axis when the first cam portion contacts the first follower portion and thereby drive the distal firing portion distally through the first segment of longitudinal travel.

4. The surgical instrument of claim 2, wherein the first follower portion comprises a first arm extending toward the first cam portion, wherein the second follower portion comprises a second arm extending toward the second cam portion.

5. The surgical instrument of claim 1, wherein the cam assembly comprises a first cam and a second cam, wherein the first cam includes the first cam portion, wherein the second cam includes the second cam portion.

6. The surgical instrument of claim 5, wherein the first and second cams are spaced apart longitudinally along a shaft driven by the motor.

7. The surgical instrument of claim 1, wherein the first and second cam portions are arranged on a shaft and extend radially outwardly from a longitudinal axis defined by the shaft, wherein the first and second cam portions are longitudinally spaced from one another along the longitudinal axis.

8. The surgical instrument of claim 7, wherein the first cam portion includes an outermost radial end defining a maximum radial dimension of the first cam portion relative to the longitudinal axis, wherein the second cam portion includes an outermost radial end defining a maximum radial dimension of the second cam portion relative to the longitudinal axis, wherein the outermost radial ends of the first and second cam portions are angularly offset from one another about the longitudinal axis.

9. The surgical instrument of claim 1, wherein the first segment of longitudinal travel is longer than the second segment of longitudinal travel.

10. The surgical instrument of claim 1, wherein the cam assembly is configured to drive the distal firing portion distally from the proximal position to the distal position by rotation of the cam assembly through a single revolution.

11. The surgical instrument of claim 1, further comprising a resilient member configured to bias the firing assembly proximally into engagement with the cam assembly.

12. The surgical instrument of claim 1, wherein the first cam portion is configured to drive the distal firing portion distally through the first segment of longitudinal travel with a first force, wherein the second cam portion is configured to drive the distal firing portion distally through the second segment of longitudinal travel with a second force, wherein the first and second forces differ in magnitude.

13. The surgical instrument of claim 1, wherein the first cam portion includes a first contoured face, wherein the second cam portion includes a second contoured face, wherein the first and second contoured faces are configured to contact the firing assembly.

14. The surgical instrument of claim 1, wherein the cam assembly comprises a barrel cam, wherein the barrel cam includes the first cam portion and the second cam portion.

15. The surgical instrument of claim 1, wherein the stapler assembly is operable to drive a plurality of staples in a circular array to secure together first and second lumens of tissue.

16. A surgical instrument comprising:
(a) a body;
(b) a shaft extending distally from the body, wherein the shaft comprises a proximal end and a distal end;
(c) a stapling assembly, wherein the stapling assembly is disposed at the distal end of the shaft, wherein the stapling assembly is operable to drive a plurality of staples into tissue;
(d) a motor;
(e) a cam assembly coupled with the motor and including a first cam and a second cam, wherein the motor rotates the first and second cams; and
(f) a firing assembly having a distal firing portion operatively coupled with the stapling assembly, wherein the distal firing portion is configured to move distally from a proximal position to a distal position and thereby drive movement of the stapling assembly,
wherein the first and second cams are configured to sequentially engage the firing assembly during rotation of the cam assembly such that:
(i) the first cam drives the distal firing portion distally with a first force through a first segment of longitudinal travel, and
(ii) the second cam drives the distal firing portion distally with a second force through a second segment of longitudinal travel that extends distally from the first segment of longitudinal travel, wherein the second force differs in magnitude from the first force,
wherein the firing assembly includes a follower member operatively coupled to the body and to the distal firing portion, wherein the follower member includes a first follower portion and a second follower portion, wherein the first cam is configured to contact the first follower portion to drive the distal firing portion distally through the first segment of longitudinal travel, wherein the second cam is configured to contact the second follower portion to drive the distal firing portion distally through the second segment of longitudinal travel.

17. The surgical instrument of claim 16, wherein the second force is greater in magnitude than the first force.

18. The surgical instrument of claim 16, wherein the follower member is pivotably coupled to the body.

19. A surgical instrument comprising:
(a) a body;
(b) a shaft extending distally from the body, wherein the shaft comprises a proximal end and a distal end;
(c) a stapling assembly, wherein the stapling assembly is disposed at the distal end of the shaft, wherein the stapling assembly is operable to drive a plurality of staples into tissue;
(d) a motor;
(e) a cam mounted on a shaft rotated by the motor such that the cam rotates about a rotation axis; and
(f) a firing assembly operatively coupled with the stapling assembly, wherein the firing assembly includes:
(i) an actuating member extending distally toward the stapling assembly, wherein the actuating member is configured to move distally from a proximal position to a distal position and thereby cause the stapling assembly to drive staples into tissue,
(ii) a follower member body pivotably coupled to the body about a pivot axis and operatively coupled to a proximal end of the actuating member, wherein the pivot axis of the follower member body and the rotation axis of the cam are nonparallel relative to each other, wherein the follower member body has a proximal end, wherein the motor is operable to rotate the cam to cause the follower member body to pivot about the pivot axis and thereby drive the actuating member toward the distal position, and
(iii) a friction reducing member arranged at the proximal end of the follower member body, wherein the friction reducing member comprises a curved surface that engages the cam.

20. The surgical instrument of claim 19, wherein the pivot axis of the follower member body is perpendicular to the rotation axis of the cam.

* * * * *